(12) United States Patent
Schwartz et al.

(10) Patent No.: US 10,881,455 B2
(45) Date of Patent: Jan. 5, 2021

(54) LESION ASSESSMENT BY DIELECTRIC PROPERTY ANALYSIS

(71) Applicants: Navix International Limited, Tortola (VG); Yitzhack Schwartz, Haifa (IL); Yizhaq Shmayahu, Ramat-HaSharon (IL); Eli Dichterman, Haifa (IL)

(72) Inventors: Yitzhack Schwartz, Haifa (IL); Yizhaq Shmayahu, Ramat-HaSharon (IL); Eli Dichterman, Haifa (IL)

(73) Assignee: Navix International Limited, Road Town (VG)

( * ) Notice: Subject to any disclaimer, the term of this patent is extended or adjusted under 35 U.S.C. 154(b) by 284 days.

(21) Appl. No.: 15/573,493

(22) PCT Filed: May 11, 2016

(86) PCT No.: PCT/IB2016/052690
§ 371 (c)(1),
(2) Date: Nov. 13, 2017

(87) PCT Pub. No.: WO2016/181318
PCT Pub. Date: Nov. 17, 2016

(65) Prior Publication Data
US 2018/0125575 A1 May 10, 2018

Related U.S. Application Data

(60) Provisional application No. 62/304,455, filed on Mar. 7, 2016, provisional application No. 62/291,065, filed
(Continued)

(51) Int. Cl.
*A61B 18/14* (2006.01)
*A61B 34/10* (2016.01)
(Continued)

(52) U.S. Cl.
CPC ........ *A61B 18/1492* (2013.01); *A61B 5/0538* (2013.01); *A61B 5/063* (2013.01);
(Continued)

(58) Field of Classification Search
CPC ...... A61B 18/1492; A61B 2018/00357; A61B 2018/00577; A61B 2018/00642;
(Continued)

(56) References Cited

U.S. PATENT DOCUMENTS

| 4,917,097 A | 4/1990 | Proudian et al. |
| 5,553,611 A | 9/1996 | Budd et al. |

(Continued)

FOREIGN PATENT DOCUMENTS

| EP | 1504713 | 2/2005 |
| EP | 1726268 | 11/2006 |

(Continued)

OTHER PUBLICATIONS

International Preliminary Report on Patentability dated Jul. 25, 2019 From the International Bureau of WIPO Re. Application No. PCT/IB2018/050195. (9 Pages).

(Continued)

*Primary Examiner* — Michael F Peffley

(57) ABSTRACT

Devices and methods for tissue lesion assessment and/or creation based on dielectric properties are disclosed. In some embodiments, one or more probing frequencies are delivered via electrodes including an electrode in proximity to a tissue (for example, myocardial tissue). Measured dielectric properties (such as impedance properties), optionally together with other known and/or estimated tissue characteristics, are used to determine the lesion state of the tissue. In some embodiments, a developing lesion state is moni- (Continued)

tored during treatment formation of a lesion (for example, ablation of heart tissue to alter electrical transmission characteristics).

51 Claims, 16 Drawing Sheets

Related U.S. Application Data on Feb. 4, 2016, provisional application No. 62/160,080, filed on May 12, 2015.

(51) Int. Cl.
  *G16H 50/50* (2018.01)
  *G16H 10/60* (2018.01)
  *G16H 30/20* (2018.01)
  *A61B 34/20* (2016.01)
  *A61B 5/06* (2006.01)
  *A61B 90/00* (2016.01)
  *A61B 18/00* (2006.01)
  *A61M 25/01* (2006.01)
  *A61B 17/00* (2006.01)

(52) U.S. Cl.
  CPC ............... *A61B 34/10* (2016.02); *A61B 34/20* (2016.02); *G16H 10/60* (2018.01); *G16H 30/20* (2018.01); *G16H 50/50* (2018.01); *A61B 90/37* (2016.02); *A61B 90/39* (2016.02); *A61B 2017/00026* (2013.01); *A61B 2018/00357* (2013.01); *A61B 2018/00577* (2013.01); *A61B 2018/00642* (2013.01); *A61B 2018/00702* (2013.01); *A61B 2018/00738* (2013.01); *A61B 2018/00761* (2013.01); *A61B 2018/00791* (2013.01); *A61B 2018/00875* (2013.01); *A61B 2018/00904* (2013.01); *A61B 2034/104* (2016.02); *A61B 2034/105* (2016.02); *A61B 2034/107* (2016.02); *A61B 2034/2046* (2016.02); *A61B 2034/2053* (2016.02); *A61B 2090/065* (2016.02); *A61B 2090/365* (2016.02); *A61B 2090/374* (2016.02); *A61B 2090/3762* (2016.02); *A61B 2090/3983* (2016.02); *A61M 2025/0166* (2013.01)

(58) Field of Classification Search
  CPC .......... A61B 2018/00702; A61B 2018/00738; A61B 2018/00761; A61B 2018/00875; A61B 2034/2046; A61B 2034/2053; A61B 5/0538; A61B 5/063; A61B 90/37; A61B 90/39
  See application file for complete search history.

(56) References Cited

U.S. PATENT DOCUMENTS

| | | | |
|---|---|---|---|
| 5,662,108 A | 9/1997 | Budd et al. | |
| 5,697,377 A | 12/1997 | Wittkampf | |
| 5,724,978 A | 3/1998 | Tenhoff | |
| 5,983,126 A | 11/1999 | Wittkampf | |
| 6,019,725 A | 2/2000 | Vesely et al. | |
| 6,038,468 A | 3/2000 | Rex | |
| 6,240,307 B1 | 5/2001 | Beatty et al. | |
| 6,317,621 B1 | 11/2001 | Graumann et al. | |
| 6,322,558 B1 | 11/2001 | Taylor et al. | |
| 6,423,057 B1 | 7/2002 | He et al. | |
| 6,515,657 B1 | 2/2003 | Zanelli | |
| 6,640,119 B1 | 10/2003 | Budd et al. | |
| 6,728,562 B1 | 4/2004 | Budd et al. | |
| 6,826,420 B1 | 11/2004 | Beatty et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,989,010 B2* | 1/2006 | Francischelli | A61B 18/1206 128/898 |
| 6,990,370 B1 | 1/2006 | Beatty et al. | |
| 7,001,383 B2* | 2/2006 | Keidar | A61B 18/1492 600/509 |
| 7,187,973 B2 | 3/2007 | Hauck | |
| 7,189,208 B1 | 3/2007 | Beatty et al. | |
| 7,306,593 B2* | 12/2007 | Keidar | A61B 5/06 606/34 |
| 7,996,060 B2 | 8/2011 | Trofimov et al. | |
| 8,403,925 B2* | 3/2013 | Miller | A61B 18/1233 606/34 |
| 8,454,589 B2* | 6/2013 | Deno | A61B 18/1492 606/34 |
| 9,743,854 B2* | 8/2017 | Stewart | A61B 5/04017 |
| 2002/0068931 A1 | 6/2002 | Wong et al. | |
| 2003/0074011 A1 | 4/2003 | Gilboa et al. | |
| 2003/0220636 A1 | 11/2003 | Bowman et al. | |
| 2004/0039278 A1 | 2/2004 | Wacker et al. | |
| 2004/0044279 A1 | 3/2004 | Lewin et al. | |
| 2004/0097805 A1 | 5/2004 | Verard et al. | |
| 2004/0147920 A1 | 7/2004 | Keidar | |
| 2004/0176804 A1 | 9/2004 | Palti | |
| 2005/0015006 A1 | 1/2005 | Mitschke et al. | |
| 2005/0033164 A1 | 2/2005 | Yatsuo et al. | |
| 2005/0054913 A1 | 3/2005 | Duerk et al. | |
| 2005/0054918 A1 | 3/2005 | Sra | |
| 2005/0245814 A1 | 11/2005 | Anderson et al. | |
| 2007/0043296 A1 | 2/2007 | Schwartz | |
| 2007/0049915 A1 | 3/2007 | Haemmerich et al. | |
| 2007/0167706 A1 | 7/2007 | Boese et al. | |
| 2007/0167726 A1 | 7/2007 | Unal et al. | |
| 2008/0114235 A1 | 5/2008 | Unal et al. | |
| 2008/0118135 A1 | 5/2008 | Averbuch et al. | |
| 2008/0125775 A1 | 5/2008 | Morris | |
| 2008/0177175 A1 | 7/2008 | Mottola et al. | |
| 2008/0183070 A1 | 7/2008 | Unal et al. | |
| 2008/0208031 A1 | 8/2008 | Kurpad et al. | |
| 2008/0221425 A1 | 9/2008 | Olson et al. | |
| 2008/0275440 A1 | 11/2008 | Kratoska et al. | |
| 2008/0275465 A1 | 11/2008 | Paul et al. | |
| 2008/0281319 A1* | 11/2008 | Paul | A61B 18/1206 606/41 |
| 2009/0015818 A1 | 1/2009 | Ikeda et al. | |
| 2009/0148012 A1 | 6/2009 | Altmann et al. | |
| 2009/0275828 A1 | 11/2009 | Shachar et al. | |
| 2009/0281566 A1 | 11/2009 | Edwards et al. | |
| 2010/0063400 A1 | 3/2010 | Hall et al. | |
| 2010/0069921 A1* | 3/2010 | Miller | A61B 18/1233 606/130 |
| 2010/0217116 A1 | 8/2010 | Eck et al. | |
| 2010/0249579 A1 | 9/2010 | Starks | |
| 2010/0274239 A1 | 10/2010 | Paul et al. | |
| 2010/0283484 A1 | 11/2010 | Cohen et al. | |
| 2010/0312094 A1 | 12/2010 | Guttman et al. | |
| 2011/0106221 A1 | 5/2011 | Neal, II et al. | |
| 2011/0230758 A1 | 9/2011 | Eichler | |
| 2012/0059249 A1 | 3/2012 | Verard et al. | |
| 2012/0109115 A1 | 5/2012 | Condie et al. | |
| 2012/0123250 A1 | 5/2012 | Pang et al. | |
| 2012/0172724 A1 | 7/2012 | Hill et al. | |
| 2012/0173217 A1 | 7/2012 | Heimbecher | |
| 2012/0197243 A1 | 8/2012 | Sherman et al. | |
| 2012/0238866 A1 | 9/2012 | Wang et al. | |
| 2013/0137980 A1 | 5/2013 | Waters et al. | |
| 2013/0272593 A1 | 10/2013 | Lee et al. | |
| 2014/0088943 A1 | 3/2014 | Trayanova et al. | |
| 2014/0187949 A1 | 7/2014 | Zhao et al. | |
| 2014/0243813 A1 | 8/2014 | Paul et al. | |
| 2014/0330111 A1 | 11/2014 | Lichtenstein et al. | |
| 2015/0141978 A1* | 5/2015 | Subramaniam | A61B 5/0538 606/34 |
| 2016/0066977 A1* | 3/2016 | Neal, II | A61B 18/18 606/34 |
| 2016/0095651 A1 | 4/2016 | Deno et al. | |
| 2016/0095653 A1 | 4/2016 | Lambert et al. | |

(56) References Cited

U.S. PATENT DOCUMENTS

| | | |
|---|---|---|
| 2017/0014181 A1 | 1/2017 | Bar-Tal et al. |
| 2017/0156792 A1 | 6/2017 | Ziv-Ari et al. |
| 2020/0022649 A1 | 1/2020 | Rodriguez et al. |
| 2020/0060757 A1 | 2/2020 | Ben-Haim et al. |

FOREIGN PATENT DOCUMENTS

| | | |
|---|---|---|
| EP | 2248480 | 11/2010 |
| EP | 2777584 | 9/2014 |
| HR | P20131208 | 3/2014 |
| JP | 2001-340336 | 12/2001 |
| JP | 2005-199072 | 7/2005 |
| JP | 2015-503365 | 2/2015 |
| WO | WO 98/01069 | 1/1998 |
| WO | WO 2007/067628 | 6/2007 |
| WO | WO 2010/102794 | 9/2010 |
| WO | WO 2013/096916 | 6/2013 |
| WO | WO 2016/135584 | 9/2016 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |
| WO | WO 2018/092071 | 5/2018 |
| WO | WO 2018/130976 | 7/2018 |

OTHER PUBLICATIONS

International Preliminary Report on Patentability dated May 31, 2019 From the International Bureau of WIPO Re. Application No. PCT/IB2017/057186. (13 Pages).
International Search Report and the Written Opinion dated Apr. 30, 2018 From the International Searching Authority Re. Application No. PCT/IB2017/057186. (22 Pages).
International Search Report and the Written Opinion dated Apr. 30, 2018 From the International Searching Authority Re. Application No. PCT/IB2018/050195. (16 Pages).
Invitation to Pay Additional Fees and Communication Related to the Results of the Partial International Search and the Provisional Opinion dated Feb. 22, 2018 From the International Searching Authority Re. Application No. PCT/IB2017/057186. (12 Pages).
Canpolat et al. "Relationship Between Vitamin D Level and Left Atrial Fibrosis in Patients With Lone Paroxysmal Atrial Fibrillation Undergoing Cryoballoon-Based Catheter Ablation", Journal of Cardiology, 6991): 16-23, Published Online Aug. 21, 2016.
Caspi et al. "Modeling of Arrhythmogenic Right Ventricular Cardiomyopathy With Human Induced Pluripotent Stem Cells", Circulation: Cardiovscular Genetics, 6(6): 557-568, Published Online Nov. 7, 2013.
Cerit et al. "Association of Pre-Ablation Level of Vitamin D With Atrial Fibrillation Recurrence After Catheter Ablation", Europace, 19(9): 1586, 01 Sep. 2017.
Jiang et al. "Association of Pre-Ablation Level of Potential Blood Markers With Atrial Fibrillation Recurrence After Catheter Ablation: A Meta-Analysis", Europace, 19(3): 392-400, Mar. 1, 2017.
McDowell et al. "Virtual Electrophysiological Study of Atrial Fibrillation in Fibrotic Remodeling", PLOS ONE, 10(2): e117110-1-e117110-16, Published Online Feb. 18, 2015.
Ranjan et al. "Gaps in the Ablation Line as a Potential Cause of Recovery From Electrical Isolation and Their Visualization Using MRI", Circulation: Arrhythmia and Electrophysiology, XP055452459, 4(3): 279-286, Published Online Apr. 14, 2011.
Shoemaker et al. "Common Genetic Variants and Response to Atrial Fibrillation Ablation", Circulation: Arrhythmia and Electrophysiology, 8(2): 296-302, Published Online Feb. 14, 2015.
Ueberham et al. "Genetic ACE 1/D Polymorphism and Recurrence of Atrial Fibrillation After Catheter Ablation", Circulation: Arrhythmia and Electrophysiology, 6(4): 732-737, Published Online Jul. 22, 2013.
Wang et al. "Association of the Angiotensinogen M235T Polymorphism With Recurrence After Catheter Ablation of Acquired Atrial Fibrillation", Journal of the Renin-Angiotensin-Aldosterone System, 16(4): 888-897, Published Online Aug. 3, 2015.
Communication Relating to the Results of the Partial International Search dated Aug. 22, 2016 From the International Searching Authority Re. Application No. PCT/IB2016/052686.
Communication Relating to the Results of the Partial International Search dated Aug. 22, 2016 From the International Searching Authority Re. Application No. PCT/IB2016/052688.
Communication Relating to the Results of the Partial International Search dated Aug. 25, 2016 From the International Searching Authority Re. Application No. PCT/IB2016/052692.
Communication Relating to the Results of the Partial International Search dated Aug. 26, 2016 From the International Searching Authority Re. Application No. PCT/IB2016/052687.
International Preliminary Report on Patentability dated Nov. 23, 2017 From the International Bureau of WIPO Re. Application No. PCT/IB2016/052686. (11 Pages).
International Preliminary Report on Patentability dated Nov. 23, 2017 From the International Bureau of WIPO Re. Application No. PCT/IB2016/052687. (10 Pages).
International Preliminary Report on Patentability dated Nov. 23, 2017 From the International Bureau of WIPO Re. Application No. PCT/IB2016/052688. (9 Pages).
International Preliminary Report on Patentability dated Nov. 23, 2017 From the International Bureau of WIPO Re. Application No. PCT/IB2016/052690. (9 Pages).
International Preliminary Report on Patentability dated Nov. 23, 2017 From the International Bureau of WIPO Re. Application No. PCT/IB2016/052692. (13 Pages).
International Search Report and the Written Opinion dated Jan. 3, 2017 From the International Searching Authority Re. Application No. PCT/IB2016/052688. (14 Pages).
International Search Report and the Written Opinion dated Oct. 12, 2016 From the International Searching Authority Re. Application No. PCT/IB2016/052686.
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Oct. 21, 2016 From the International Searching Authority Re. Application No. PCT/IB2016/052687. (16 Pages).
International Search Report and the Written Opinion dated Aug. 25, 2016 From the International Searching Authority Re. Application No. PCT/IB2016/052690.
Anter et al. "Evaluation of a Novel High-Resolution Mapping Technology for Ablation of Recurrent Scar-Related Atrial Tachycardias," Heart Rhythm, 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Black-Maier et al. "Risk of Atrioesophageal Fistula Formation With Contact-Force Sensing Catheters", HeartRhythm, 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Chierchia et al. "An Initial Clinical Experience With a Novel Microwave Radiometry Sensing Technology Used in Irrigated RF Ablation for Flutter", Academic Hospital Brussels, Belgium, 1 P. Jan. 1, 2011.

(56) References Cited

OTHER PUBLICATIONS

Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PVI Lines to Incorporate Non-PV Targets Identified by Pre-Ablation Mapping with the AcQMap System: Update on the Uncover-AF Trial," EP Lab Digest, 17(5), May 2017, 5 pages.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA, May 9-12, 2012, Session: Role of Autonomics in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # PO3-53, May 10. 2012.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summer for Public Disclosure", St. Jude Medical, Section 12, 6 P., Aug. 29, 2013.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.
St. Jude Medical "Cardiac Mapping System / ECG. NSite™ NavX™", St. Jude Medical, Products Sheet, 22 P., 2017.
Vandekerckhove et al. "Flutter Ablation With an Irrigated Catheter Using Microwave Radiometry Sensing Technology: First Report in Men", Sint Jan Hospital, Department of Cardiology, Bruges, Belgium, 1 P., Jan. 1, 2011.
Wang et al. "Microwave Radiometric Thermoetry and Its Potential Applicability to Ablative Therapy", Journal of Interventional Cardiac Electrophysiology, 4(1): 295-300, Feb. 2000.
Wittkampf et al. "LocaLisa: New Technique for Real-Time 3-Dimensional Localization of Regular Intracardiac Electrodes", Circulation, 99(10): 1312-1317, Mar. 16, 1999.
Zhong et al. "On the Accuracy of CartoMerge for Guiding Posterior Left Atrial Ablation in Man", Heart Rhythm, 4(5): 595-602, Published Online Feb. 9, 2007.
Notice of Reasons for Refusal dated Apr. 21, 2020 From the Japan Patent Office Re. Application No. 2017-558702 and Its Translation Into English. (16 Pages).

* cited by examiner

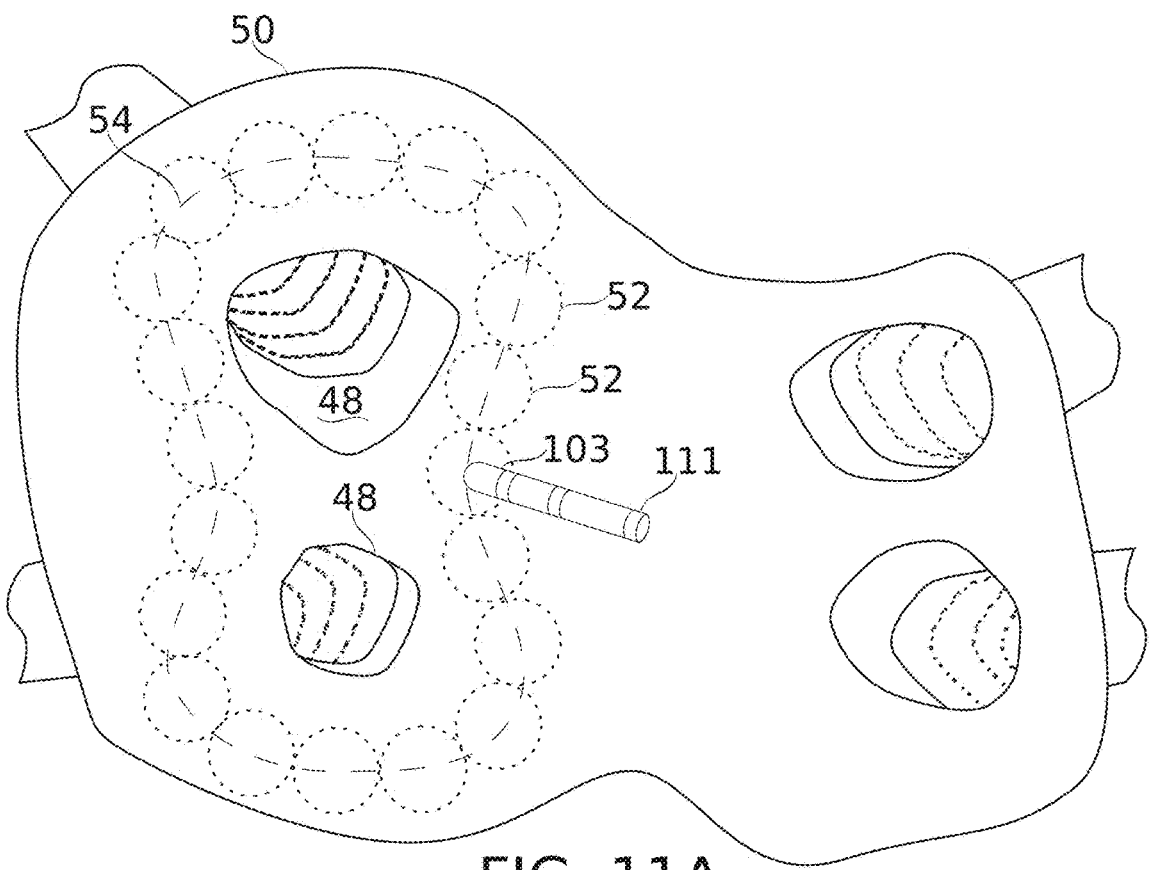
FIG. 11A
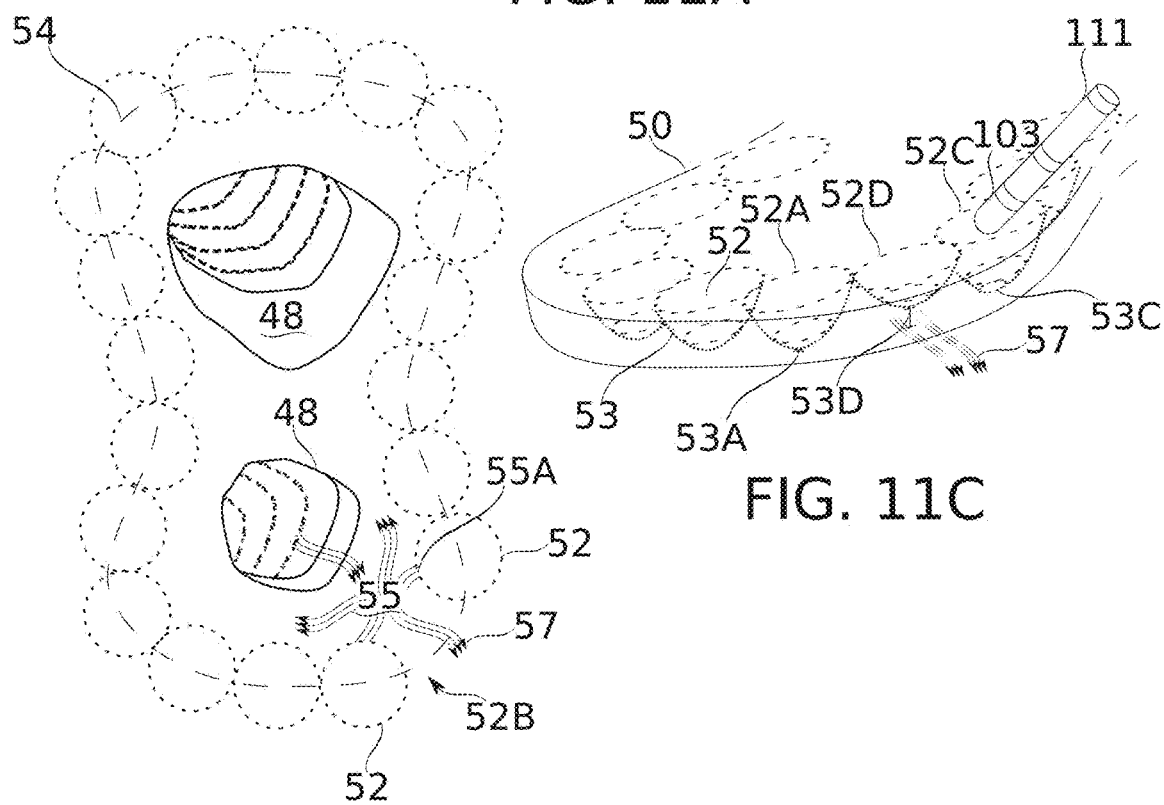
FIG. 11C
FIG. 11B

LESION ASSESSMENT BY DIELECTRIC PROPERTY ANALYSIS

RELATED APPLICATIONS

This application is a National Phase of PCT Patent Application No. PCT/IB2016/052690 having International filing date of May 11, 2016, which claims the benefit of priority under 35 USC § 119(e) of U.S. Provisional Patent Application Nos. 62/160,080 filed May 12, 2015; 62/291,065 filed Feb. 4, 2016; and 62/304,455 filed Mar. 7, 2016. The contents of the above applications are all incorporated by reference as if fully set forth herein in their entirety.

PCT Patent Application No. PCT/IB2016/052690 is also related to PCT Patent Application Nos. PCT/IB2016/052687, titled "SYSTEMS AND METHODS FOR TRACKING AN INTRABODY CATHETER", PCT/IB2016/05268866142 titled "CALCULATION OF AN ABLATION PLAN", PCT/IB2016/052692 titled "FIDUCIAL MARKING FOR IMAGE-ELECTROMAGNETIC FIELD REGISTRATION", and PCT/IB2016/052686 titled "CONTACT QUALITY ASSESSMENT BY DIELECTRIC PROPERTY ANALYSIS", all having International filing date of May 11, 2016, the contents of which are incorporated herein by reference in their entirety.

FIELD AND BACKGROUND OF THE INVENTION

The present invention, in some embodiments thereof, relates to systems and methods for planning, production, and/or assessment of tissue lesions, and, more particularly, but not exclusively, to planning, production, and/or assessment of tissue lesions by use of sensing from intra-body electrodes.

RF ablation probes are in use for minimally invasive ablation procedures, for example, in the treatment of cardiac arrhythmia. A high frequency alternating current (e.g., 350-500 kHz) is introduced to a treatment region through the probe, creating an electrical circuit involving tissue, which heats up as it absorbs energy of the applied electrical field. Suitably controlled, the heating results in effects such as tissue ablation. In the control of cardiac arrhythmia, a goal of ablation is to create lesions in a pattern which will break pathways of abnormal electrophysiological conduction which contribute to heart dysfunction (such as atrial fibrillation).

One variable affecting the heating is the frequency-dependent relative permittivity K of the tissue being treated. The (unitless) relative permittivity of a material (herein, K or dielectric constant) is a measure of how the material acts to reduce an electrical field imposed across it (storing and/or dissipating its energy). Relative permittivity is commonly expressed as $$\kappa = \varepsilon_r(\omega) = \frac{\varepsilon(\omega)}{\varepsilon_0},$$

where $\omega = 2\pi f$, and f is the frequency (of an imposed voltage or signal). In general, $\varepsilon_r(\omega)$ is complex valued; that is: $\varepsilon_r(\omega) = \varepsilon'_r(\omega) + i\varepsilon''_r(\omega)$.

The real part $\varepsilon'_r(\omega)$ is a measure of energy stored in the material (at a given electrical field frequency and voltage), while the imaginary part $\varepsilon''_r(\omega)$ is a measure of energy dissipated. It is this dissipated energy that is converted, for example, into heat for ablation. Loss in turn is optionally expressed as a sum of dielectric loss $\varepsilon''_{rd}$ and conductivity $\sigma$ as $$\varepsilon''_r(\omega) = \varepsilon''_{rd} + \frac{\sigma}{\omega \cdot \varepsilon_0}.$$

Any one of the above parameters: namely $\kappa$, $\varepsilon$, $\varepsilon'_r$, $\varepsilon''_r$, $\sigma$, and/or $\varepsilon''_{rd}$, may be referred to herein as a dielectric parameter. The term dielectric parameter encompasses also parameters that are directly derivable from the above-mentioned parameters, for example, loss tangent, expressed as tan $$\sigma = \frac{\varepsilon''_r}{\varepsilon'_r},$$

complex retractive index, expressed as $n = \sqrt{\varepsilon_r}$, and impedance, expressed as $$Z(\omega) = \sqrt{\frac{i\omega}{\sigma + i\omega\varepsilon_r}} \quad (\text{with } i = \sqrt{-1}).$$

Herein, a value of a dielectric parameter of a material may be referred to as a dielectric property of the material. For example, having a relative permittivity of about 100000 is a dielectric property of a 0.01M KCl solution in water at a frequency of 1 kHz, at about room temperature (20°, for example). Optionally, a dielectric property more specifically comprises a measured value of a dielectric parameter. Measured values of dielectric parameters are optionally provided relative to the characteristics (bias and/or jitter, for example) of a particular measurement circuit or system. Values provided by measurements should be understood to comprise dielectric properties, even if influenced by one or more sources of experimental error. The formulation "value of a dielectric parameter" is optionally used, for example, when a dielectric parameter is not necessarily associated with a definite material (e.g., it is a parameter that takes on a value within a data structure).

Dielectric properties as a function of frequency have been compiled for many tissues, for example, C. Gabriel and S. Gabriel: *Compilation of the Dielectric Properties of Body Tissues at RF and Microwave Frequencies* (web pages presently maintained at www(dot)niremf(dot)ifac(dot)cnr(dot)it/docs/DIELECTRIC/home(dot)html).

Dielectric properties comprise certain measured and/or inferred electrical properties of a material relating to the material's dielectric permittivity. Such electrical properties optionally include, for example, conductivity, impedance, resistivity, capacitance, inductance, and/or relative permittivity. Optionally, dielectric properties of a material are measured and/or inferred relative to the influence of the material on signals measured from electrical circuits. Optionally, dielectric properties of a material are measured and/or inferred relative to the influence of the material on an applied electric field. Measurements are optionally relative to one or more particular circuits, circuit components, frequencies and/or currents.

Microscopically, several mechanisms potentially contribute to electrically measured dielectric properties. For example, in the kHz-MHz range, movement of ionic charge carriers generally dominates. In many tissues, cellular membranes play a significant role in the compartmentalization of ionic charges. Conductance pathways are also potentially influenced by the cellular structure of a tissue. Dielectric properties optionally are influenced by and/or take into account non-dielectric properties such as temperature.

SUMMARY OF THE INVENTION

There is provided, in accordance with some exemplary embodiments, a method of tissue assessment in vivo, comprising: determining at least one dielectric property of a target tissue by analysis of signals sensed at an electrode positioned intra-body; and estimating a tissue state, based on the determined dielectric property.

According to some embodiments, the tissue state indicates a state of a lesion formed by tissue ablation.

According to some embodiments, the signals comprise signal output from an electrical circuit comprising the electrode, the electrode being positioned at an intra-body position wherefrom the electrode acts in establishing an electrical field intersecting the target tissue.

According to some embodiments, the estimating is further based on estimated anatomical information for tissue affecting the signal output.

According to some embodiments, the estimating is further based on the received data structure.

According to some embodiments, the data structure is obtained by machine learning methods.

According to some embodiments, the at least one dielectric property comprises a vector of dielectric parameter values, and the estimating is based on statistical correlation between vectors of dielectric parameter values and the tissue state, the statistical correlation being described by the data structure.

According to some embodiments, the method comprises indicating the tissue state from the estimating.

According to some embodiments, the determining and the estimating are performed iteratively, during ablating in the target tissue.

According to some embodiments, the ablating is controlled based on the estimating.

According to some embodiments, the electrode at the intra-body position acts in performing the ablating.

According to some embodiments, the method comprises reducing or terminating the ablating based on the estimating indicating an elevated risk of an adverse event associated with ablating.

According to some embodiments, the ablating comprises formation of a lesion in cardiac tissue for the treatment of atrial fibrillation.

According to some embodiments, the estimating comprises prediction of a state of the target tissue, the state predicted to be that state of the target tissue brought about after the ablating is performed according to the parameters of the ablating; and the parameters of the ablating are adjusted so that the predicted state of the target tissue matches a target state of the target tissue after ablation.

According to some embodiments, the method comprises ablating the target tissue to produce the target state, according to the planning.

According to some embodiments, the tissue state comprises at least one from a group consisting of: a physiological tissue property, an anatomical tissue property, and a functional tissue property.

According to some embodiments, the tissue state comprises at least one from a group consisting of: a lesion depth, a lesion volume, a degree of lesion transmurality, a characterization of tissue edema, a characterization of functional inactivation, a classification as to a potential for tissue charring, and a classification as to a potential for steam pop.

There is provided, in accordance with some exemplary embodiments, a method of tissue assessment, comprising: receiving a data structure correlating values of dielectric parameters with values of at least one parameter of a tissue state; determining a value of at least one dielectric parameter of a target tissue, based on signal output from an electrical circuit comprising at least one electrode positioned intra-body and in proximity to the target tissue; estimating a value of at least one parameter of a tissue state, based on the determined value of the at least one dielectric parameter of the target tissue and the received data structure; and providing a feedback indicative of the estimate.

According to some embodiments, the target tissue comprises lesioned tissue.

According to some embodiments, the data structure is obtained by machine learning methods.

According to some embodiments, the determining and the estimating are performed iteratively, during ablating in the target tissue.

According to some embodiments, the ablating is terminated, based on the estimating.

According to some embodiments, at least one parameter of the ablating is varied, during the ablating, based on the estimating.

According to some embodiments, the controlled at least one parameter of the ablating includes at least one from a group consisting of: a duration of the ablating, a power supplied for the ablating, a frequency used for the ablating, selection of an electrode for the ablating.

According to some embodiments, the controlled at least one parameter of the ablating includes a rate of ablation.

According to some embodiments, the ablating is performed through the at least one electrode positioned intra-body and in proximity to the target tissue.

According to some embodiments, the method comprises reducing or terminating the ablating based on the estimating indicating an elevated risk of an adverse event associated with ablating.

According to some embodiments, the adverse event is tissue charring or fluid vaporization.

According to some embodiments, the ablating comprises formation of a lesion in cardiac tissue for the treatment of atrial fibrillation.

According to some embodiments, the determining and the estimating are performed before at least a portion of a protocol for ablating of the target tissue is performed; the estimating comprises prediction of a value of the at least one parameter of a tissue state, the value predicted as being brought about after the portion of the ablating protocol is performed; and the estimating is further based on parameters of the protocol for ablating.

According to some embodiments, the feedback comprises an indication of a likelihood of successfully achieving a target lesion result under conditions on which the estimating is based.

According to some embodiments, the feedback comprises preventing onset of the ablating.

According to some embodiments, the feedback comprises providing the adjusted protocol for use in controlling further ablating.

According to some embodiments, the method comprises ablating of a portion of the target tissue.

According to some embodiments, the determining and the estimating are performed after ablating of a portion of the target tissue to form a lesion.

According to some embodiments, the feedback comprises indication of a gap within the lesion formed by the ablating.

According to some embodiments, the target tissue comprises a myocardial wall, and the gap comprises a region where the lesion is incompletely transmural.

According to some embodiments, the gap comprises a region which is not irreversibly lesioned, the region being at least 1.3 mm across.

According to some embodiments, the feedback comprises an estimate of the irreversibility of lesioning in a region of the ablating.

According to some embodiments, the at least one parameter of a tissue state comprises a lesion depth.

According to some embodiments, the at least one parameter of a tissue state comprises a lesion volume.

According to some embodiments, the value of at least one dielectric parameter comprises a vector of values, and the estimating is based on statistical correlation between vectors of dielectric parameter values and the at least one parameter of a tissue state, the statistical correlation being described by the data structure.

According to some embodiments, the estimating is further based on estimated anatomical information for tissue affecting the signal output of the electrical circuit.

According to some embodiments, the determining comprises analysis of frequency response behavior of the signal output of the electrical circuit.

According to some embodiments, the providing comprises providing feedback to control an ablation device.

According to some embodiments, the data structure comprises values of dielectric parameters determined according to a type of the target tissue.

There is provided, in accordance with some exemplary embodiments, a system for tissue assessment, comprising: at least one electrode on an intra-body catheter, positionable to be in proximity to a target tissue; an electrical field measurement device configured to measure parameters of an output signal of an electrical circuit comprising the at least one electrode and the target tissue, measurements of the output signal parameters including measurements of the values of dielectric parameters of the target tissue; and an analyzer module, including a data structure correlating values of dielectric parameters of tissue with a tissue state; wherein the analyzer module is configured to receive the measurements of dielectric parameters of the target tissue, and to produce from them an estimate of a state of the target tissue, based on the data structure.

According to some embodiments, the analyzer is also configured to receive additional information relating to at least one from a group consisting of: the anatomy of tissue comprised in the electrical circuit, a position of the intra-body catheter, and a position of a skin patch electrode.

According to some embodiments, the analyzer module is configured to provide the estimate of the state of the target tissue to the ablation controller; and wherein the ablation controller is configured to control ablation by the ablation probe based on the estimated state of the target tissue.

According to some embodiments, the at least one electrode positionable on an intra-body catheter also acts as the ablation probe. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof.

A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 11A-11C schematically illustrate aspects of lesioning to block of tissue conduction, for example for the treatment of atrial fibrillation, according to some embodiments of the present disclosure;

DESCRIPTION OF SPECIFIC EMBODIMENTS OF THE INVENTION

Figure 1A:
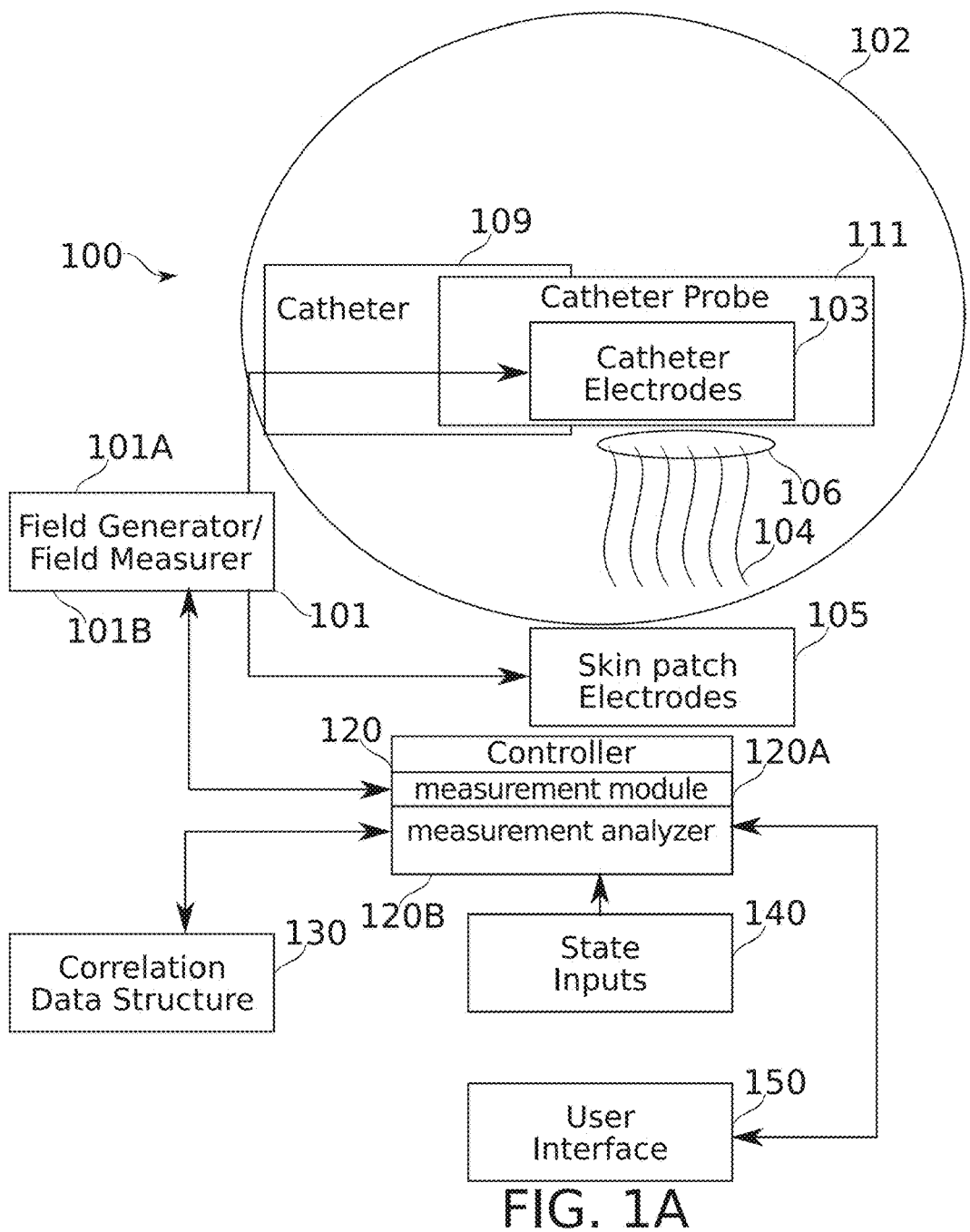
FIG. 1A schematically illustrates a system for the measurement of tissue dielectric properties, according to some embodiments of the present disclosure.

The present invention, in some embodiments thereof, relates to systems and methods for planning, production, and/or assessment of tissue lesions, and, more particularly, but not exclusively, to planning, production, and/or assessment of tissue lesions by use of sensing from intra-body electrodes.

Overview

An aspect of some embodiments of the invention relates to ablation of tissue under feedback control of dielectric property measurements relating to ablation progress.

In some embodiments of the invention, measured dielectric properties of a tissue region are related to properties known and/or expected for such a tissue region (for example, through a data structure describing previously determined correlations), and the relating used in planning, delivery, and/or assessment of a treatment to that tissue. In some embodiments, the treatment delivered comprises ablating of the tissue (for example, ablating to form a lesion and/or to remove a tumor or other abnormal growth). In some embodiments, measured dielectric properties of tissue are used to determine if an ablation lesion meets one or more targeted criteria. For example, in the case of treatment for atrial fibrillation, it is optionally determined if a lesioned region of tissue is of sufficient size, continuity, and/or degree of tissue transformation (such as by scarring and/or cellular disruption) to produce an irreversible block of impulse conduction. Optionally, the ablation is by catheter ablation; for example: RF ablation, cryoablation, ultrasound ablation, laser ablation, electroporating ablation, or another form of ablation.

A potential advantage of using dielectric property measurements in conjunction with RF ablation, in particular, is that the same electrode (and/or electrode probe) can optionally be used for both delivery of ablation energy, and for providing of electrical fields used to assess tissue targeted for ablation and/or ablated tissue.

Optionally, the tissue to be ablated is a region of atrial wall, for example, regions of the left atrial wall around the pulmonary veins for treatment of atrial fibrillation. Optionally, other tissue is ablated, for example, heart muscle to remove outflow blockage occurring in hypertrophic obstructive cardiomyopathy, neural tissue for treatment by neuromodulation, cancerous tissue for oncological treatment, another tissue, or one of these tissues for a different treatment purpose.

In some embodiments, a parameter of ablation is selected during ablation based on dielectric property measurements. Optionally, the parameter of ablation varies iteratively during the ablation. Examples of ablation parameters include duty cycle, total duration, frequency, and/or power level. An aspect of some embodiments of the invention relates to determination of ablation parameters based on dielectric property measurements made pre-ablation.

Dielectric property measurements are made, for example, based on the frequency response characteristics (for example, characteristics of frequency-dependent impedance, resonances, and/or phase delays) of output signals measured from an electrical circuit comprising a target tissue.

In some embodiments, dielectric property measurements are made before ablating (for example, to form a lesion, and/or to remove a tumor or other abnormal growth), to determine an initial condition which potentially affects the ablation outcome and/or targeted outcome. In some embodiments, measured dielectric properties of tissue are used to determine if an ablation lesion meets and/or will meet one or more targeted criteria. For example, in the case of treatment for atrial fibrillation, it is optionally determined how to lesion a region of tissue so that it comprises sufficient size, continuity, and/or degree of tissue transformation (such as scarring and/or cellular disruption) to produce an irreversible block of impulse conduction. For example, the dielectric property measurement is optionally related (e.g., via previously established calibration data), to a tissue thickness or quality of tissue contact by a probe electrode. Optionally, a parameter of ablation (for example, a duration or power level) is chosen according to a relative tissue thickness correlated with a dielectric property measurement—for example, in some embodiments where a target is to achieve a transmural lesion, a longer duration or higher power level is chosen for ablation of a thicker muscle wall. In some embodiments, a parameter of ablation is selected to reflect a quality of the ablation conditions, and ablation optionally proceeds only if conditions are appropriate. For example, where a dielectric property measurement reflects relatively poor or intermittent contact with a target tissue, ablation is optionally prevented and/or a device operator receives a warning that current ablation conditions are associated with a risk of an inadequate outcome.

An aspect of some embodiments of the invention relates to assessment of ablation effects based on dielectric property measurements made post-ablation.

In some embodiments, treatment ablations (for example, to form a lesion and/or to remove a tumor or other abnormal growth) are potentially associated with one or both of reversible and irreversible effects. In cardiac muscle, for example, a potentially reversible effect comprises inactivation of excitability and/or signal transmission. Resumption of signal transmission upon recovery from such inactivation can lead to treatment failure, when the targeted outcome is permanent blockage of transmission. In some embodiments, dielectric measurements potentially reveal underlying structural changes which prevent effect reversal (or reveal their absence). For example, cellular membrane integrity and/or fluid channel formation potentially affect charge movements underlying aspects of dielectric measurements. These potentially also reflect the integrity of cellular structure which is needed in order for reversal of functional inactivation.

In some embodiments, a relationship between dielectric measurements and lesion irreversibility is established by observed correlations. For example, a data structure is compiled comprising separate measurements of dielectric properties and of associated lesion results (optionally, this data structure describes a particular electrode configuration, for example an electrode or electrode array which is used for ablating); then subsequent dielectric property measurements are compared to this data structure, and/or analyzed according to associative rules generated from this data structure, in order to determine an associated assessment of lesion reversibility in one or more lesioned locations. Optionally, the data structure is structured as a database. Optionally, dielectric property measurements are made post-ablation to verify that changes associated with irreversible lesioning have occurred. Optionally, the measurements comprise comparison of post-ablation measurements with pre-ablation measurements.

In some embodiments, a treatment target is a continuous region of ablation. Optionally, a treatment target in atrial fibrillation is formation of a continuous ablation line (for example, a ring around a pulmonary vein). Additionally or alternatively, the treatment target is formation of a fully transmural lesion. In some embodiments of the invention, dielectric properties of an ablation region are mapped by multiple electrode placements and/or electrode dragging, such that there is a high confidence of detecting any gap in the ablation pattern which potentially can lead to reconnection across the lesion. In some embodiments, the maximum permissible gap is, for example, about 1.0 mm, about 1.3 mm, about 1.5 mm, or another larger, smaller, or intermediate gap. An aspect of some embodiments of the invention relates to detection and/or anticipation of undesirable occurrences based on dielectric properties.

Examples of undesirable occurrences include, for example, "steam pop" (local fluid vaporization) or charring. These events are potentially adverse, in that they lead to an elevated risk of complication (for example, heart wall perforation). In some embodiments, dielectric profiles are determined (for example, based on calibration preparations) which correlate with such adverse condition. Optionally, one or more dielectric profiles are determined to correspond to conditions preceding development of such adverse conditions. Optionally, upon detection of such a dielectric profile of an adverse condition, one or more corrective recourses are taken, for example: halting lesioning, warning an operator, reducing a power level, or another corrective action to reduce a rate of ablation. Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

It should be understood that examples of dielectric property-based tissue assessment—even where described with respect to a specific tissue such as cardiac tissue—are optionally applied, changed as necessary, to dielectric assessment of other tissues; for example: neural tissue, tumor tissue (for example, cancer), other abnormal growth tissue such as warts, skin tissue, mucous membrane, or another tissue. It should also be understood that tissue assessment is optionally not limited to applications used as examples such as pre-lesioning, during lesioning, and/or post-lesioning assessment of tissue. Optionally, dielectric assessment (changed from specifics of the examples as necessary) comprises, for example, characterization of a tissue type, state, extent, and/or other tissue property.

System for Measurement of Dielectric Properties

Figure 1B:
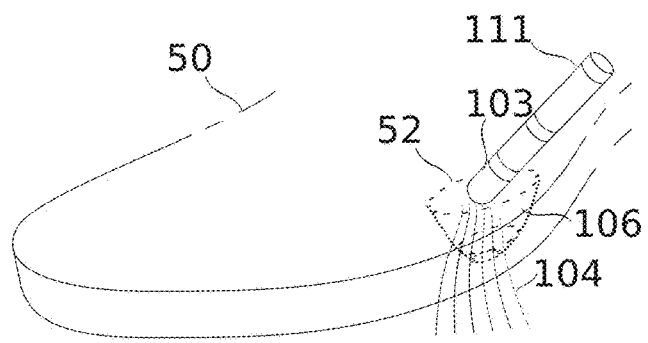
FIG. 1B shows a probe of the system of FIG. 1A in proximity to a target tissue, according to some embodiments of the present disclosure.

Reference is now made to FIG. 1A, which schematically illustrates a system 100 for the measurement of tissue dielectric properties, according to some exemplary embodiments of the present disclosure. Reference is also made to FIG. 1B, which shows a probe 111 of the system 100 in proximity to a target tissue 106, according to some exemplary embodiments of the present disclosure.

In some embodiments, dielectric properties of tissue are assessed for detecting, planning, creating, and/or assessing of tissue lesions. In some embodiments, assessed lesions comprise lesions made for treatment, for example, of atrial fibrillation, hypertrophic obstructive cardiomyopathy, neuromodulation, and/or tumors (e.g., cancerous tumors). Dielectric property measurements are made, for example, based on the frequency- and/or time-dependent response characteristics of an electrical circuit comprising a target tissue. In some embodiments, circuit response characteristics comprise output signals (e.g. changes in voltage potential) in response to one or more driving inputs.

In some embodiments, system 100 comprises an electrical field measurement device 101B, connected to a set of catheter electrodes 103, and a set of skin-patch electrodes 105 to measure properties (for example, voltage potential and how it changes) of time-varying electrical field 104 therebetween. The electrical field is generated by a field generator 101A; optionally included together in a combined electrical field generation/measurement device 101. In some embodiments, a catheter probe 111 comprising the catheter electrodes 103 is introduced to the region of a tissue to be ablated (a target tissue region 106) by means of a catheter 109. For measurement, catheter electrodes 103 are optionally placed in a proximity to the target region close enough to select it for sensing. In some embodiment, selection for sensing comprises positioning the electrode where it acts in establishing an electrical field intersecting the target region. Preferably (and particularly if the same electrode is also to be used for ablation) contact is made, but some degree of optional separation is potentially compatible with sufficient proximity to isolate of dielectric properties; for example, up to 1 mm, 2 mm, 3 mm, or another larger, smaller, or intermediate distance from the target region. In some embodiments, the skin patch electrodes are externally applied, for example, to the body of a patient. As a result, field 104 is induced in tissue 102 (for example, tissue of a patient's body) separating the catheter electrodes 103 and the skin patch electrodes 105. Optionally, the electrical field also extends through a target tissue region 106. Target region 106 is optionally targeted for one or both of lesion assessment and/or ablation (lesion formation). Giving a schematic perspective view of some of the elements of FIG. 1A, FIG. 1B shows targeting by catheter probe 111 and electrode 103 of a target tissue region 106 for assessment and/or creation of a transmural lesion 52 in a tissue region 50 (for example, a cardiac wall). The view is similar to that of FIG. 11C. As described, for example, in relation to FIG. 2, measurements of frequency-dependent impedance in the electrical circuit(s) resulting from this configuration reflect electrical properties of tissue through which the electrical field extends (in particular, dielectric properties). The dielectric properties of the tissue in turn are affected, for example, when tissue undergoes lesioning.

Optionally, the number of catheter electrodes is 2, 3, or 4 electrodes. Optionally, a greater or lesser number of catheter electrodes is used.

Optionally, the number of skin patch electrodes is 4, 5, or 6 electrodes. Optionally, a greater or lesser number of skin patch electrodes is used.

Optionally, the characteristics of the time-varying electrical field 104 are chosen to be appropriate to a measurement function which is to be performed. Typically (for measurement functions), the frequencies of the electrical field used are in the range of 40 kHz to 2 MHz. Optionally, the number of frequencies used is 10 or fewer frequencies. Optionally, the frequencies are distributed (for example, distributed evenly) throughout the full range of frequencies chosen. Optionally, frequencies chosen are concentrated in some particular frequency range. For example, for lesion assessment, frequencies in the upper portion of this range are optionally used (for example, frequencies in the range of 1 MHz to 2 MHz). Applied voltages are preferably in the safe range for use in humans, for example, 100-500 millivolts, and/or a current of 1 milliamp or less (a typical body resistance is about 100Ω). Resulting field strengths are in the range, for example of a few millivolts per centimeter; for example, 5 mV/cm, 10 mV/cm, 20 mV/cm, or another larger, smaller, or intermediate value. Based on requirements for data acquisition, sensing time is optionally about 10 msec per measurement (or a longer or shorter period, for example, about 100 msec, or 1 second), for embodiments including fast automated switching of frequencies and/or electrode pairs.

Figure 3:
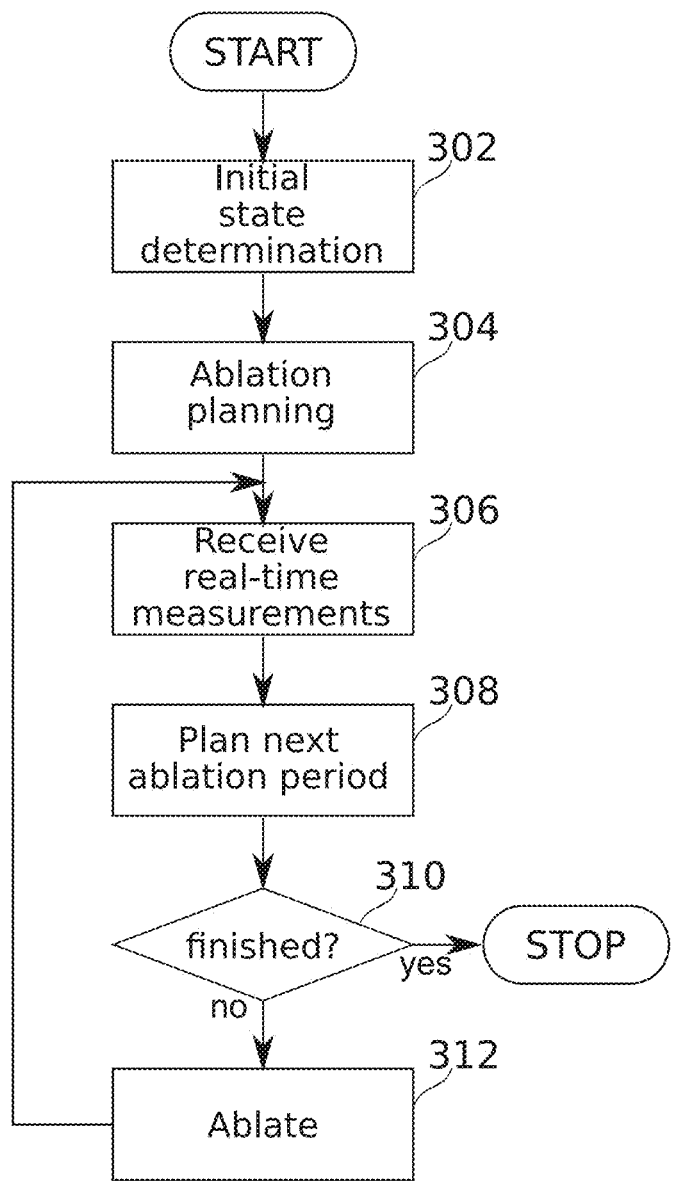
FIG. 3 is a flowchart of a method for planning, creation, and/or evaluation of an ablation lesion with respect to parameters such as volume, depth, and/or irreversibility, according to some embodiments of the present disclosure.

In some embodiments, a method of correlation is optionally used to relate measured electrical properties (dielectric-related properties in particular) of tissue to lesion results (such a method is explained, for example, in relation to FIG. 3). It can be understood that any sufficiently dense sampling of frequencies may be initially measured with respect to a particular system and set of tissue conditions to determine which frequencies show the most useful results. The reduction to a number practical for field use can be based on which frequencies yield data having the greatest statistical correlation with results. It has been found by the inventors that ten or fewer frequencies, distributed, for example, within the range of 40 kHz to 2 MHz, are useful to allow tissue assessment (for example, lesion size assessment). In some embodiments, for example, a set of frequencies chosen for measurement includes 40 kHz, 100 kHz, 700 kHz, 1 MHz, 1.2 MHz, and/or 1.7 MHz.

It should be noted that published permittivity and conductivity values of many tissues, including heart, are roughly linear in log:log plots over ranges of a few hundred kHz within the range mentioned, which potentially allows distinctions among tissue types to be made without a requirement for dense frequency sampling.

In some embodiments, catheter probe 111 is optionally used for ablation by RF ablation energies delivered through the catheter electrodes 103 which are also used for measurements. Optionally, catheter electrodes 103 are provided as part of a standard catheter probe, operated with a system capable of driving, sensing and/or analyzing circuits so as to acquire data suitable for dielectric property analysis.

In some embodiments, other electrodes, another catheter probe and/or another ablation device and/or method is used, for example, a device or method for cryoablation, ultrasound ablation, laser ablation, electroporating ablation, or another form of ablation.

In some embodiments, the electrical field generation and/or electrical field measurement device 101A, 101B is under the control of controller 120, which itself is optionally under user control through user interface 150. Controller 120 optionally comprises a computer with CPU or other digital hardware operating according to programmed code. Controller 120 is described herein as a multi-functional module; however, it is to be understood that functions of controller 120 are optionally distributed among two or more modules of the system. For example, controlling of hardware elements used in dielectric measurement is optionally performed by a measurement module 120A.

Electrical field generation by device 101, for example, to probe dielectric properties of tissue by means of impedance measurements, may be under the control of controller 120. Measurements from device 101, for example, of impedance properties used in measuring dielectric properties, are communicated back to controller 120. In some embodiments, controller 120 is also (directly or indirectly) an ablation controller. Ablation is optionally via electrical fields (e.g., RF electrical fields) generated by device 101, or by another ablation device, for example as described herein.

In some embodiments, controller 120, is also a measurement analyzer 120B (optionally, a separate measurement analyzer is provided), relating measurements to one or more additional parameters. For example, state inputs provided at 140 optionally comprise any state relevant to the measurements, including, for example, position(s) of catheter electrode 103 and/or skin patch electrodes 105; and/or details of the anatomy of tissue 102 and/or target region 106. In some embodiments, details of anatomy comprise image data giving tissue types in positions through which field 104 is induced. Optionally, details of anatomy comprise a dielectric property model of the anatomy, for example, dielectric properties inferred from image data and/or typical dielectric properties of different tissue types. Optionally, the dielectric property model is refined by additional data received by electrode sensing, for example, sensing from catheter electrodes 103 and/or skin patch electrodes 105. In some embodiments, user interface 150 is provided with controls and/or displays for governing how controller 120 uses available state inputs—for example, to review and/or correct data-to-model registration, adjust model parameters, and the like. Optionally, user interface 150 comprises one or more controls (graphical or hardware, for example) and/or displays for making adjustments by the manipulation of numeric and/or slider position entries, option lists, tables, adjustable graphs or images, or another control, display, or combined control/display element.

Optionally, system 100 comprises correlation data structure 130, functionally connected with controller 120. Optionally, correlation data structure 130 is part of controller 120. In some embodiments, the correlation data structure 120 comprises data by which measured electrical field properties (in particular, those associated with dielectric properties of target tissue) are linked to other tissue parameters of interest. Tissue parameters of interest optionally include parameters reflecting lesioning for target tissue 106 and/or its vicinity. Tissue parameters optionally include depth, volume, and/or extent of tissue, optionally lesioned tissue in particular. Optionally, other parameters of lesioned tissue are measured. Optionally, tissue parameters may comprise classification as to one or more lesioned or un-lesioned tissue types or states, such as normal, scarred, permanently or reversibly inactivated, edematous, and/or charred. Herein, a tissue state (or state of a tissue), should be understood to comprise a selection of functional, physiological and/or anatomical tissue properties; that is, values (numbers or classifications, for example) of one or more functional, physiological and/or anatomical parameters of the tissue; and for example, one or more of those just listed. Optionally, the parameters of the tissue state are non-dielectric parameters. Where discussion in vector terms applies, a tissue state may be understood as a state vector having values for one or more parameters as components. This understanding should also apply, changed as necessary, to use of the terms "lesion state" or "state of a lesion".

The linkage is optionally (for example) by statistical correlation (for example, using techniques of computational statistics), by use of equations fit (for example, by mathematical optimization) to correlation data, and/or by use of a machine learning technique. In some embodiments, a machine learning technique used comprises one or more implementations of decision tree learning, association rule learning, an artificial neural network, inductive logic programming, a support vector machine, cluster analysis, Bayesian networks, reinforcement learning, representation learning, similarity and metric learning, and/or another technique taken from the art of machine learning.

In some embodiments, correlations are supplemented by modeling of the effects of one or more physical properties: for example, temperature, and/or time-varying filling with fluid (such as blood) and/or gas (such as air). In some embodiments, the data structure is compiled by the application of one or more of such linkage methods to previously recorded calibration data. For example, lesions are formed for use in calibration, and separate measurement of dielectric properties and corresponding lesion sizes (and/or other lesion state information, such as lesion type and/or condition) are performed. Optionally, additional data, for example, state data (for example, provided by state inputs 140), is also incorporated into the data structure.

In some embodiments, the relationships among measurements are determined, and stored by correlation data structure 130 in such a way that a vector of dielectric properties from field generator/measurement device 101, optionally supplemented by information from state inputs 140, can be used to estimate other lesion properties in the data structure 130 such as for lesion size (e.g., lesion depth, width, and/or volume), and/or type or condition (e.g., reversible, irreversible, transmural, fibrotic, and/or edematous). In some embodiments, a lesion property is continuously variable, for example, a size measurement. In some embodiments, a lesion property comprises a category assignment—for example, the lesion is estimated as belong within one of a plurality of lesion depth categories. In some embodiments, a lesion property comprises a qualitative state assessment; for example, "transmural", "irreversible", and/or "edematous". Optionally, a property is associated with an estimate of likelihood; for example, a standard deviation and/or a confidence level.

In some embodiments, a lesion property comprises an aspect of a shape of the lesion. Lesion depth, for example, is optionally estimated within a range up to about 4 mm, 6 mm, 8 mm, 10 mm, or another larger, smaller, or intermediate depth. Optionally lesion depth is estimated with respect to a total wall thickness; for example, 70%, 80%, 90%, 100%, or another lesser or intermediate degree of transmurality. Optionally, lesion shape includes assessment of the presence of a gap along a lesion extent. In some embodiments, a maximum permissible gap is, for example, about 1.0 mm, about 1.3 mm, about 1.5 mm, or another larger, smaller, or intermediate gap.

In some embodiments, a lesion property comprises an aspect of tissue structure in the region of the lesion. Optionally, dielectric properties are used to distinguish between the tissue structural states of healthy tissue and fibrotic tissue. Optionally, dielectric properties are used to distinguish between tissues having intact or disrupted cellular membrane structures. Optionally, dielectric properties are used to distinguish between edematous and non-edematous tissue.

In some embodiments, a lesion property comprises an aspect of tissue function in the region of the lesion. For example, a region of tissue is distinguished between states which are or are not electrophysiologically active, and/or between states which are actively contractile, or not.

Overview of Dielectric Tissue State Assessment

Figure 12:
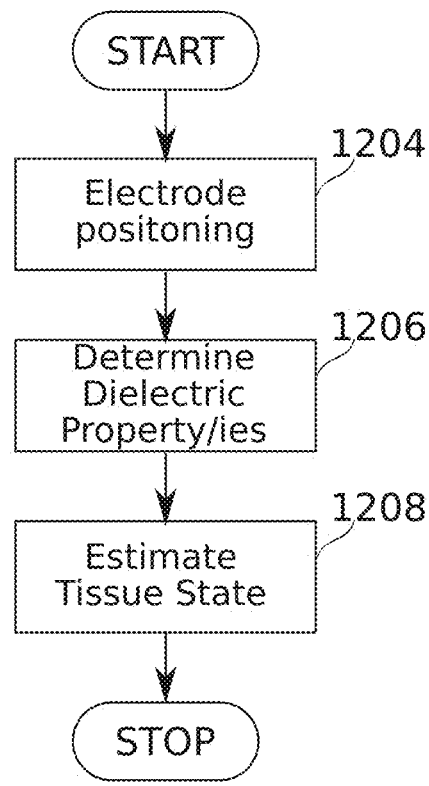
FIG. 12 is a flowchart overviewing a method for assessing an anatomical, physiological, and/or functional tissue state based on one or more dielectric properties of the tissue, according to some embodiments of the present disclosure.

Reference is now made to FIG. 12, which is flowchart overviewing a method for assessing an anatomical, physiological, and/or functional tissue state based on one or more dielectric properties of the tissue, according to some exemplary embodiments of the present disclosure.

At block 1204, in some embodiments, the method begins with positioning of an intra-body electrode 103. In some embodiments, the electrode is positioned at an intra-body position wherefrom the electrode acts in establishing an electrical field 104 intersecting the target tissue 106. The intra-body electrode 103 optionally acts together with a second electrode 105 which is outside the body, for example, placed on the body surface (a body surface electrode). Optionally, the second electrode is another intra-body electrode 103.

At block 1206, in some embodiments, one or more dielectric properties of the target tissue are determined, for example by operation of field generator 101A and field measurement device 101B. Examples of the determination of dielectric properties are detailed, for example, in relation to blocks 206 and 208 of FIG. 2, herein.

At block 1208, in some embodiments, a property of an anatomical, physiological, and/or functional tissue state is estimated (examples of such states are described, for example, in relation to FIGS. 1A-B), based on the determined dielectric properties. In some embodiments, the estimating comprises access by a digital computer to a data structure 130 which describes correspondences (for example, correlations between dielectric properties and tissue states that co-occur with them. Optionally, the data structure is produced by use of a machine learning technique, or another method, for example as also described in relation to FIGS. 1A-B and 2. Optionally, additional state inputs 140 (for example, inputs describing aspects of patient anatomy, or other inputs as described herein in relation to state inputs 140) are used in the estimating.

Measurement of Dielectric Properties

Figure 2:
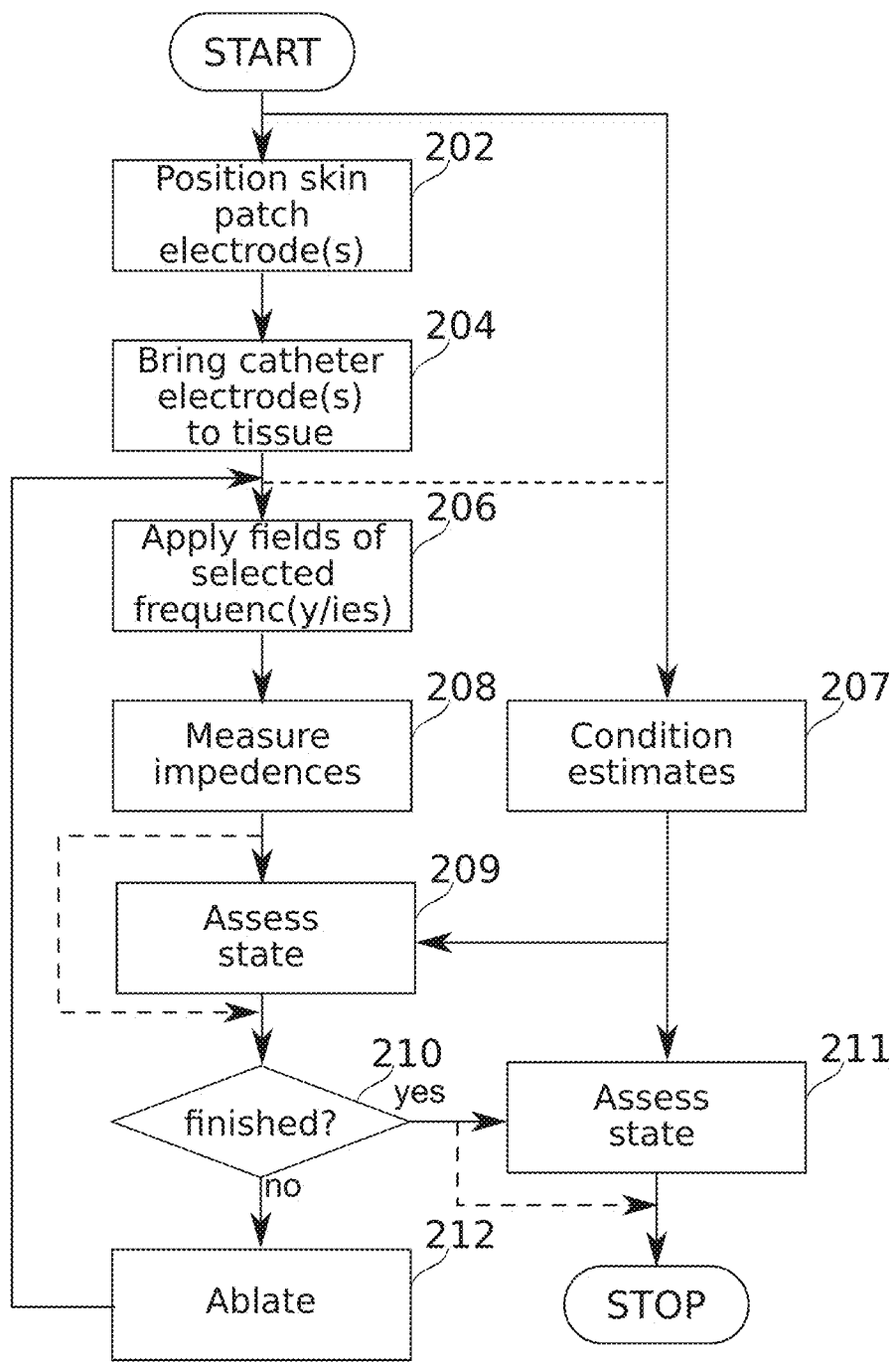
FIG. 2 is a flowchart of a method for the measurement of tissue dielectric properties, optionally in relation to other condition parameters, for measurement and/or estimation of tissue lesion properties, according to some embodiments of the present disclosure.

Reference is now made to FIG. 2, which is a flowchart of a method for the measurement of tissue dielectric properties, optionally in relation to other condition parameters, for measurement and/or estimation of tissue lesion properties, according to some exemplary embodiments of the invention.

FIG. 2 optionally applies to either of two phases of measurement—measurement for calibration, or measurement for lesion or other tissue property assessment.

Before stepping through the blocks of FIG. 2 in detail, there is now provided a brief overview of impedance measurement. To describe a basic measurement of impedance, the following notation is used:

W—A set of frequencies.
C—A set of catheter electrodes.
P—A set of patch electrodes.

Parameters and/or values for each of the above are, for example, as described in relation to FIGS. 1A-B.

Impedance measurements are optionally expressed as: $Z(t) = \{Z_{w,c,p}(t) | w \in W, c \in C, p \in P\}$ where $Z(t)$ is the complex impedance (resistance and reactance) measured at time t and frequency $\omega$ between a catheter electrode c and a patch electrode p.

Correlation information from any single electrode pair and/or frequency is generally not a sufficient basis on which to draw conclusions. It is a potential advantage to have numerous vector components (for example, measurements at multiple frequencies between multiple electrode pairs) in order to extract sufficiently strong correlations to allow lesion assessment, and/or other tissue property assessment. Optionally, the number of catheter electrodes is 2, 3, or 4 electrodes, or a greater or lesser number of catheter electrodes. Optionally, the number of skin patch electrodes is 4, 5, or 6 electrodes, or a greater or lesser number of skin patch electrodes. Optionally, between 2-10 frequencies are used (in which the electrical field is applied), or a greater number of frequencies.

Herein, determination and application of correlations between impedance measurements and tissue property assessment is described in terms of vectors, for convenience of presentation. It should be understood that in some embodiments, correlations are additionally or alternatively obtained, expressed, and/or used in another form. In some embodiments, a machine learning technique is used to establish correlations; for example: one or more implementations of decision tree learning, association rule learning, an artificial neural network, inductive logic programming, a support vector machine, cluster analysis, Bayesian networks, reinforcement learning, representation learning, similarity and metric learning, and/or another technique taken from the art of machine learning. Optionally, the choice of technique influences the storage, expression, and/or retrieval of correlation data. For example, correlations are optionally established and/or read-out by use of a machine learning paradigm expressed as an artificial neural network expressed in terms of connected nodes and connection weights. In some embodiments, determined correlations are expressed in terms of associative rules; for example, one or more functions (optionally fitted to the calibration data). In some embodiments, correlations are expressed in terms of one or more dielectric profiles. For example, a dielectric profile is defined which corresponds with the occurrence of a particular state (e.g., scarring, charring, temperature, or lesion transmurality). Optionally, profile is defined based on observations during calibration indicating that the particular state correlates with one or more impedance measurements occurring within one or more corresponding ranges. These ranges are optionally established as a dielectric profile that serves as an indication of the particular state when it is observed.

Use of multiple impedance measurements potentially assists in the isolation of correlations between impedance measurements and local tissue properties. For example, it can be considered that a substantially common tissue region near each catheter electrode $c_i$ contributes to the impedance $Z(t)$ measured between each pair of electrodes $(c_i, (p_i, \ldots p_m))$. This common region potentially increases correlation in impedance measurements made between each of those electrode pairs.

Conversely, the impedance contributions of tissue more distant from the electrode probe, separating the electrode probe and any given patch electrode $p_j$ are potentially encoded in correlations between each of the pairs $((c_1 \ldots c_n), p_j)$.

Even though the impedance interactions of the different tissues (near-catheter and far-from-catheter) are potentially non-linear in their combined effects on measurements, it can be understood based on the foregoing how contributions of local and distant tissue are potentially separable from one another based on correlation properties. Optionally, correlations are derived from changes occurring over time. For example, actual lesion state is correlated to a degree of change in dielectric measurements which occurs during to lesioning.

Features of tissue which affect impedance potentially include, for example:
  the cellular organization of the tissue, which separates charges into compartments that break down upon lesioning;
  the fibrous organization of the tissue, which also is potentially modified, for example, by denaturing of proteins upon lesioning; and/or
  temperature, which, in some embodiments, undergoes a transient change during lesioning (for example, during RF ablation lesioning), which is potentially associated with a temperature dependent change in dielectric properties.

For example, reactance (i.e., the imaginary component of measured impedance) at high frequencies is relatively lower at ablated locations, compared to non-ablated regions. This potentially reflects loss and/or disorganization of charge-separating membranes in ablated tissue. In some embodiments, changes in tissue mobility induced by lesioning are detected as a reduction in the variability (for example, heart-cycle dependent variability) of dielectric measurements.

In some embodiments, dielectric properties (e.g., impedance properties) originally observed to correlate with changes in tissue are later used as markers of these changes. More particularly, the inventors have observed correlations among measurements of impedance and measurements of lesion size and/or severity; determined, tested, and/or validated by methodologies of statistical inference, for example, using artificial neural network and/or other machine learning tools.

Referring now to block 202 of FIG. 2, in some embodiments, skin patch electrodes are positioned on the body of a patient, in good electrical contact therewith. Optionally, the patch electrodes are, for example, about 5-15 cm across. This configuration is used, for example, in connection with actual treatment of a patient.

Figure 6A:
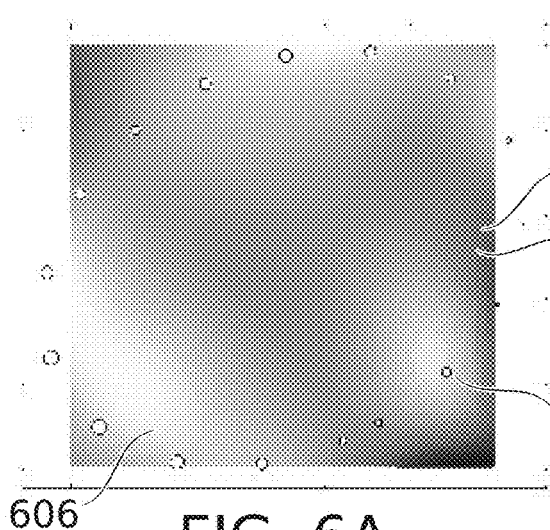
FIGS. 6A-6T show pairs comprising surface dielectric measurement plots alongside photographs of corresponding lesion patterns, in accordance with some embodiments of the present disclosure.
Figure 6B:
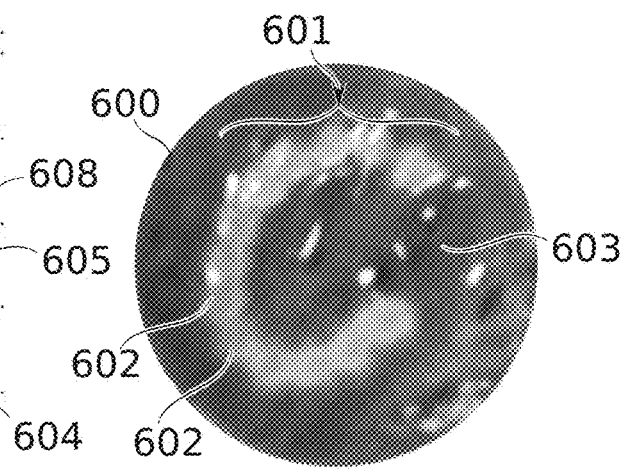
Figure 6C:
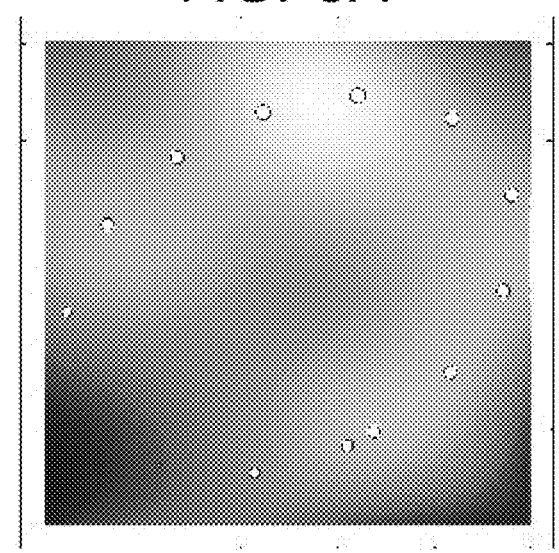
Figure 6D:
Figure 6E:
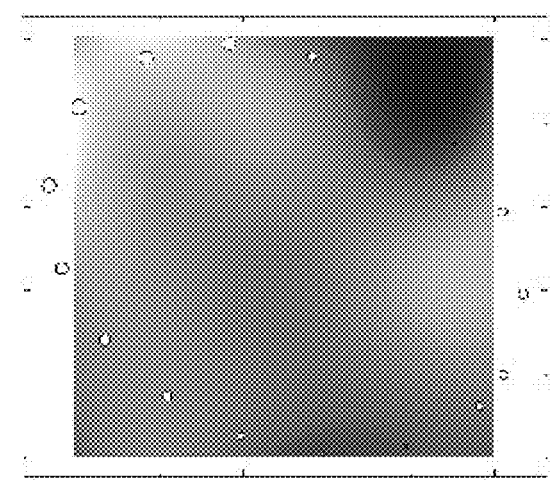
Figure 6F:
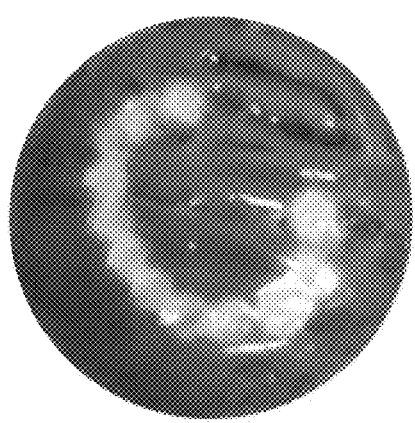
Figure 6G:
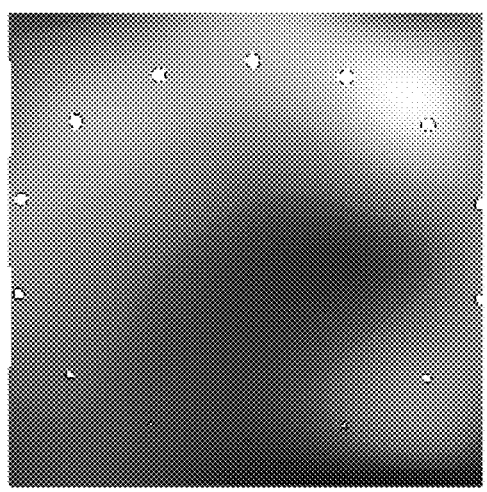
Figure 6H:
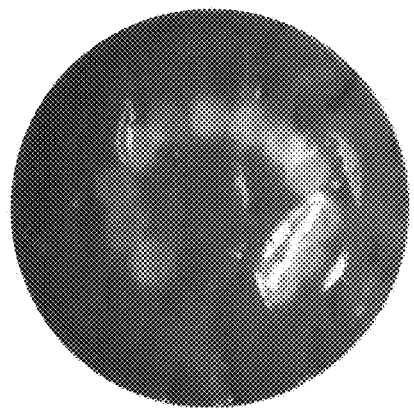
Figure 6I:
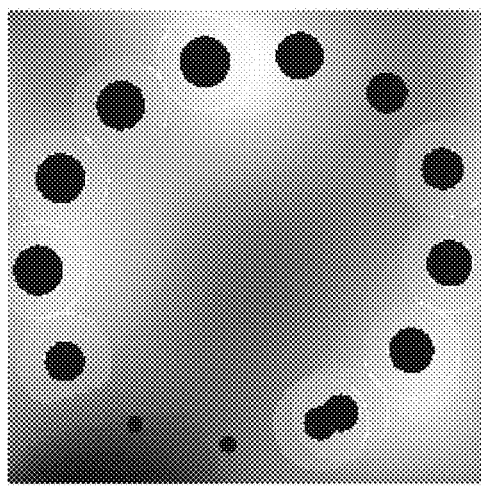
Figure 6J:
Figure 6K:
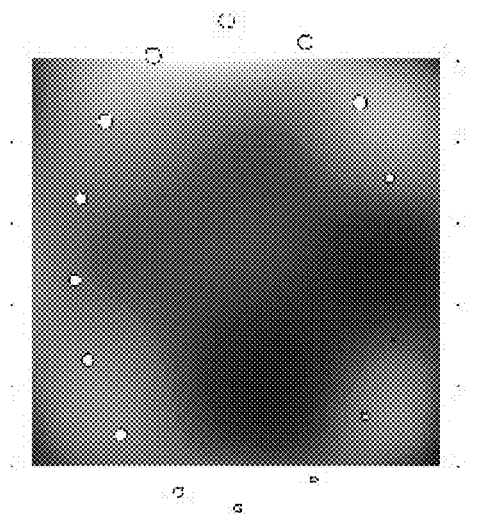
Figure 6L:
Figure 6M:
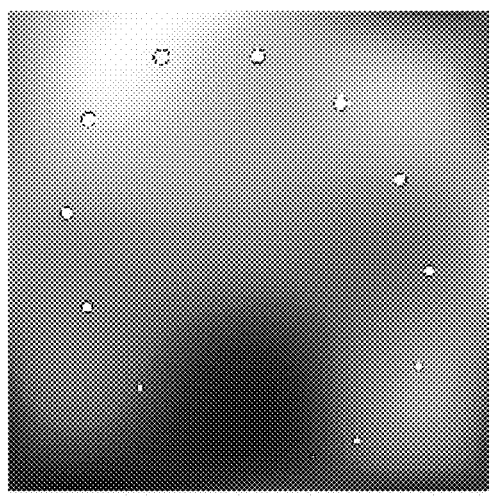
Figure 6N:
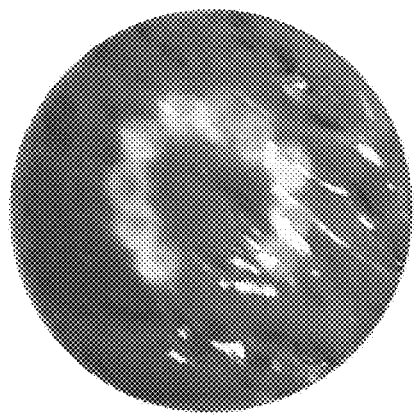
Figure 6O:
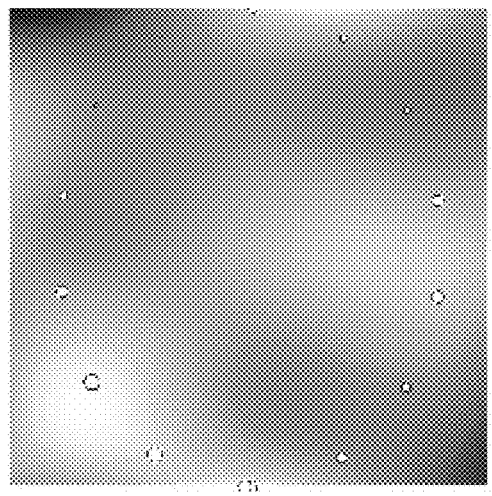
Figure 6P:
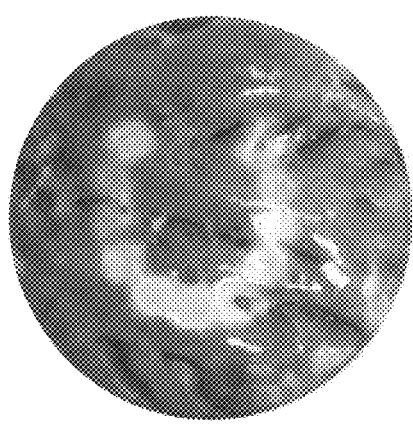
Figure 6Q:
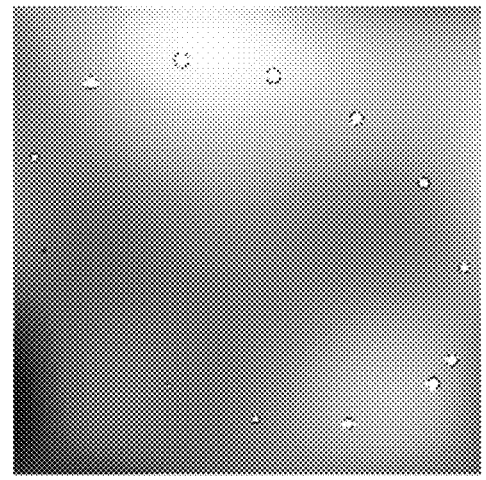
Figure 6R:
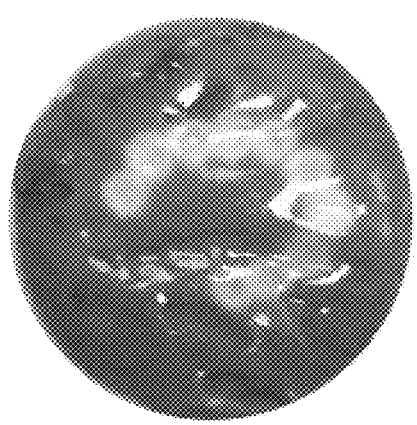
Figure 6S:
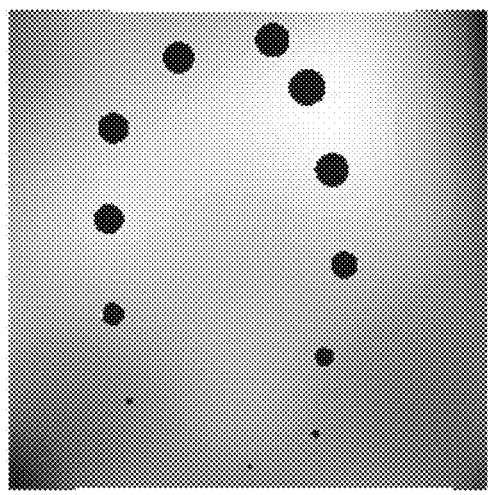
Figure 6T:

Alternatively, in some embodiments, electrodes are configured for use with a calibration sample (examples of calibration samples are shown and discussed, for example, in relation to FIGS. 6A-6T).

At block 204, in some embodiments, catheter electrodes are brought into position, for example, by navigation through a catheter to a tissue region (for example, left atrium) at which lesions exist and/or are to be created.

For use with a calibration preparation, robotic positioning is optionally used, for example as described in relation to FIGS. 6A-6T.

At block 206, in some embodiments, fields of selected frequencies are applied between catheter electrodes C and skin patch electrodes (or other electrodes, for example, as used in calibration) P. Optionally, fields are applied between one or more pairs of catheter electrodes C. Measurements of the field (for example by field measurer 101B) comprise a characteristic signal at each frequency, and for each electrode selection, which is measured at block 208 to produce the set of impedance measurements $Z(t)$. Optionally, the characteristic signal comprises an impedance measurement, and/or another measurement of a dielectric parameter.

Optionally, at block 209, and/or at block 211, a state assessment is made. An assessed state is, for example, a lesion property such as size. State assessment may refer to lesion assessment or other tissue property assessment. The state assessment is optionally for calibration and/or measurement. For example:

In some embodiments (for example, when data is being collected for a calibration data structure 130 relating dielectric properties to states of tissue), the state is assessed directly (e.g., a state comprising the geometry of a lesion is directly measured). This information is optionally used to determine a statistical correlation between impedance and/or impedance changes, and the state and/or changes in that state. Trials optionally include one or both of in vivo data, and ex vivo data, for example as described in relation to FIGS. 6A-6T, and other figures herein. Calibration data is optionally acquired under a range of conditions, with respect to a range of ablation results. Optionally acquisition occurs more than once for each condition/result, to help manage variability and measurement noise.

Additionally or alternatively, in some embodiments, state assessment comprises a state being estimated based on previously observed correlations between impedance measurements and that state.

Optional state assessment at block 209 optionally represents on-line assessment, for example, assessment during lesioning which comprising estimation of a state (e.g., a lesion state, or a state of other tissue) based on observed properties related to dielectric properties (e.g., impedance properties), and/or direct observation of the lesion state (where applicable; for example, viewing of a lesioned tissue sample preparation for calibration). Optional state assessment at block 211 represents off-line assessment (for example, for determination of tissue state for use in compiling calibration data); for example, histological tissue examination or assessment by in vivo medical imaging.

In some embodiments, other parameters (for example, state inputs 140) associated with conditions associated with the measured impedances are brought in from estimates and/or measurements made (before, after, and/or during the impedance measurement) at block 207 to produce a state assessment at block 209.

In some embodiments, recorded data (for example, comprising impedance and associated condition data) is expressed as a time series such as: $X(t)=(Z(t), A(t))$, $t=t_0, t_1, t_2, \ldots$, wherein $X(t)$ represents all measurements as a function of conditions and measurements, $Z(t)$ is the impedance component of the measurements, and $A(t)$ represents associated conditions of the impedance measurements, for example, known anatomical attributes, other prior information, or other simultaneously determined information (for example, organ type, and measurement location).

Another vector $Y(t)$ describes an assessment of the state of the tissue.

The assessed state can include tissue properties that result from the ablation procedure (e.g., lesion depth, width, volume, and/or type), and/or which indicate a possible adverse event. Adverse events include, for example, wall penetration, char, and/or steam pop. Calibration of the procedure comprises, for example, statistical analysis and/or machine learning which determines correlations between separately determined states of $Y(t)$ and $X(t)$. In application, these correlations are used to select likely existing states described by $Y(t)$ based on observed states of $X(t)$.

In some embodiments, the assessed state $Y(t)$ relates to the size and/or shape of a lesion. For example, a lesion in a cardiac wall is assessed for a depth, volume, and/or width. Optionally, the state which is assessed comprises a parameter such as lesion depth along a range of positions along a tissue wall. Optionally, depth is expressed as "transmurality"—the degree to which a lesion crosses a tissue wall (for example, fully transmural or not, or a fraction of fully transmural such as 70%, 80%, 90%, 100%). Optionally, a lesion is assessed for contiguity, and/or near-contiguity. For example, a ring-shaped lesion is assessed for gaps (optionally, gaps comprising insufficiently transmural regions). In some embodiments, the gaps are assessed relative to a threshold for a gap that potentially allows transmission to cross the gap. For example, a value of 1.3 mm as a sufficiently small gap to block transmission has been reported for some conditions, for example, by Ranjan et al. in *Circ. Arrythmia Electrophysiol.* 2011; 4:279-286).

In some embodiments, another state is assessed. For example, ablation energies potentially produce undesirable effects such as charring, and/or localized boiling (sometimes called "steam pop"). In some embodiments, tissue impedance changes continue to occur past the targeted point of tissue ablation, leading up to conditions (for example, temperatures) where an undesirable event potentially occurs. In some embodiments, impedance changes before reaching targeted ablation condition indicate a danger of such undesirable effects (for example, a change which is too fast potentially indicates that thermal energy is not being adequately dispersed either to achieve good lesion depth, or to prevent steam pop).

In some embodiments, collection of data and/or procedure calibration includes association (for example by correlation) of lesioning (ablation) parameters $L(t)$ with resulting changes to impedance measurement $\Delta Z(t)$, optionally as part of $\Delta X(t)$, and/or with the absolute values of $Z(t)$, optionally as part of $X(t)$. Optionally, ablation parameters $L(t)$ are associated with the lesion result vectors $Y(t)$ and/or their changes $\Delta Y(t)$.

In some embodiments, these associations are used to generate a repertoire of ablation parameters which are available for navigating between a current measured state $X(t)$ and a next state $X(t+1)$, and/or target state $X(t+i)$. Where predicted and achieved results vary, the parameters controlling ablation can optionally be adjusted to get "back on the path", and/or a new pathway to a targeted state can be determined.

In some embodiments, ablation parameters (for example, parameters for an electrophysiology ablation method such as RF ablation) are chosen to achieve a targeted condition, and/or avoid an adverse condition.

Parameters include, for example, delivery within a specified time, or range of times; delivery with a specified power, or range of powers; delivery with a specified frequency, or range of frequencies; selection of a rate of ablation; and/or selection of electrode(s) for use in ablation.

An example of a target in ablation treatment of atrial fibrillation is creation of a permanent, transmural fibrotic scar, positioned (for example, by encircling one or both pulmonary veins) to interrupt conductance from a source of contraction-inducing trigger impulses. Typically, ablation parameters include selection of a targeted pattern of ablation comprising a number of foci; for example, foci arranged to form a continuous extent of ablation that acts as a block between a triggering region and a trigger-receiving region. Optionally or alternatively, lesioning comprises dragging an ablation probe along a planned boundary.

Typically targeted time of ablation (for each of an optional plurality of ablation foci) is, for example, within about 10-30 seconds, 10-40 seconds, 10-60 seconds, or within another range of times having the same, higher, lower, and/or intermediate values. When heating tissue to ablate, for example by RF ablation, typical power delivery is, for example, about 10 W, 20 W, 30 W, 35 W, or another larger, smaller, or intermediate value. Typical radio frequencies used with RF ablation are, for example, in the range of about 460-550 kHz; and commonly about 500 kHz. It is to be understood that optionally, another ablation modality is used.

In some embodiments, parameters are chosen and/or changed during ablation to avoid adverse conditions such as charring or steam pop, and/or to ablate appropriately according to characteristics of the current tissue target, for example, tissue thickness. It is a potential advantage for a system to provide feedback which adds monitoring and/or flexibility to an ablation protocol. For example, heart atrial walls potentially vary considerably in thickness, for example, within a range of from 1-6 mm. This variation can sometimes be found within a single atrium. During an ablation protocol, achieving transmural ablation uses more or less ablation energy depending on wall thickness. However, over-ablation can potentially lead to damage such as heart perforation, lesioning of the esophagus, and/or lesioning of phrenic nerve fibers. In some embodiments, a thinner tissue wall leads to measurably different dielectric characteristics sensed by a probe electrode (compared to a thicker wall), potentially allowing adjustment of ablation parameters to suit target conditions. Additionally or alternatively, wall thickness is determined according to an anatomical measurement (for example, computerized analysis of MRI and/or CT image data), and thickness data provided as inputs to the determination of lesion parameters.

In some embodiments, one or more of the above ablation parameters and/or requirements are fixed (for example, by a preset and/or by user selection). Optionally, other parameters adjusted to achieve the targeted result. Optionally adjustment comprises changing one or more parameters of an ongoing ablation. Additionally or alternatively, adjustment comprises halting ablation upon reaching an end-point condition, for example, a target ablation level, or a potentially unsafe condition such as target tissue overheating.

In some embodiments, options are presented to the user as a palette of modes including one or more of:
  M-mode (manual), wherein power level is fixed, and overall ablation time is varied, according to the choice of the operator;
  A-mode (auto-mode), wherein a user limits choices to outcome goals, and the path to reach that goal is determined automatically by the system;
  T-mode (time-mode), wherein the time for ablation is fixed (or fixed within some range), and the system varies power to match;
  P-mode (power-mode), wherein the power is fixed (similar to M-mode), and other parameters, such as time, are automatically varied to achieve the targeted result.

Returning to the associated conditions of block 207: the relationship between impedance and the assessed state of the tissue is potentially affected by other conditions of the impedance measurement. Optionally, these conditions are determined at the beginning of the procedure (for example, based on previously acquired images and/or previous modeling). Additionally or alternatively, these conditions are updated during the procedure, for example, based on measurements of motion and/or position.

Examples of such conditions include the compositions and/or thicknesses of tissues nearby and/or tissues between two electrodes, the quality of electrode contact, and/or movement of tissue (for example, due to contraction of the heart and/or respiration). In some embodiments, condition information comprises a position of an electrode. In some embodiments, a position of an electrode is known and/or inferred based on navigational information, for example, from radiographic imaging, and/or determination of the position of an electrode within an electrical field.

In some embodiments, the time history of associated conditions is taken into account; for example, oscillations as a function of heartbeat and/or respiration, and/or maximum/minimum values recently recorded.

At block 210, in some embodiments, a determination is made as to the continuation of the procedure. For example, in a feedback-controlled ablation procedure, the state assessed at block 209 is used to determine if ablation (or additional ablation) is to be performed. Alternatively, in some embodiments, the determination is determined by following a protocol designed to acquire calibration data. In some embodiments, cycle loops without ablation continue for some time after the procedure completes, for example, to monitor how dielectric properties of a lesion change over time, and/or to allow dielectric measurements at different positions.

At block 212, in some embodiments, ablation is optionally performed. The ablation is optionally performed partially or completely. In some embodiments, a sequence of loops through blocks 206-212 is performed with additional and/or continuing ablation performed during each loop, until a finishing condition causes the loop to exit at block 210. Alternatively, ablation is performed in a single period without feedback control. In some embodiments, whether or not to ablate during a particular loop is determined based, for example, on an estimate of contact quality, or a determination of time history of the ablation (for example, whether a lesion is developing at the expected rate). The ablation optionally continues during a subsequent loop where appropriate conditions are restored.

In some embodiments, ablation parameters themselves (for a single shot, or for the next incremental phase of ablation) are determined based on conditions (block 207), states (block 209) and/or impedances (block 208). For example, previously determined associations between lesion size and impedance values may indicate that a greater or lesser delivery of ablation energy to the tissue is required.

In some embodiments, ablation (heating energy, for example) is delivered through the same electrode(s) or some of the electrode(s) used for measurement of impedance values reflecting the dielectric properties of the tissue, e.g., as RF energy at a frequency inducing appropriate "resistive" losses in the tissue which result in tissue heating. It is a potential benefit to ablate and measure using the same electrodes. For example, it can result in less instrumentation required, less positioning coordination required, and/or a more direct relationship between measurements made and results achieved. Additionally or alternatively, in some embodiments, measurements and ablation are performed by separate instruments (e.g., different electrodes). As also mentioned hereinabove, ablation is optionally by any ablation method known.

Lesion Assessment

Reference is now made to FIG. 3, which is a flowchart of a method for planning, creation, and/or evaluation of a lesion with respect to parameters such as volume, depth, and/or irreversibility, according to some exemplary embodiments of the invention.

Optionally, the lesion is to be formed by ablation of tissue, for example, to produce a therapeutic effect. In procedures for ablation, it is a potential advantage to be able to
  estimate in advance how to induce a lesion so that selected lesion properties are achieved,
  determine during ablation how a lesion is evolving, allowing adjustment of ablation parameters in real time, and/or
  estimate after ablation what lesion result has been achieved.

In the case of ablation to treat atrial fibrillation, the following are optional target lesion considerations:
  Selective destruction—myocardial tissue comprises both functional and mechanical properties. Ablation optionally aims to destroy certain functional characteristics (in particular, the transmission of electrical impulses among muscle cells), while leaving significant mechanical strength intact. Histologically, this potentially manifests as "coagulation necrosis", wherein membrane-defined and/or cytoplasmic structures are largely destroyed, but fibrous structures are retained (potentially in altered form, for example, partially denatured). Coagulation necrosis can be contrasted, for example, with liquefaction necrosis, which leaves behind fluid-filled spaces largely devoid of original structural elements.

Transmurality—a lesion should extend sufficiently through the thickness of a myocardial wall to block contractile impulse transmission across the position of the lesion. In some embodiments, lesions are preferably transmural, but without compromising (puncturing or unduly weakening) the mechanical integrity of the wall.

Contiguity—the full extent of lesioning should extend along a region of myocardial wall (e.g., between foci) without gaps large enough to allow myocardial pulse transmission to cross it. Maximum acceptable gap size in some embodiments is, for example, less than 1.3 mm.

In practice, lesions are optionally formed from a chain of lesion foci. For example, in an atrial wall, foci are arranged alongside each other so that they link to a continuous region of functional blockage (e.g., preventing myocardial electrical impulse transmission across it). One (but not the only) typical lesion geometry targeted in ablation procedures is a ring of merged lesion foci surrounding an atrial opening into a pulmonary vein; with a typical aim of blocking transmission of signals arising from the region of the vein and/or vein opening which can lead to atrial fibrillation.

A lesion focus can arise by ablation spreading from a fixed contact region, or by another method such as dragging an ablation electrode across a surface. Each lesion focus is potentially spatially inhomogeneous. For example, it is optionally initiated at a center (for example, a region of ablation electrode contact), from which ablation energies spread. Additionally or alternatively, a moving focus during ablation can result in inhomogeneities as a result of speed of motion, quality of contact, tissue characteristics, or another parameter. Over-ablation at some region potentially causes a problem such as structural weakness (potentially leading to leak or rupture), while under-ablation can result in insufficient functional blockage (potentially leading to failure of the lesion intervention).

In some embodiments, dielectric lesion assessment distinguishes between tissue which can potentially recover from a period of lesioning, and tissue which is permanently destroyed. For example, functional transmission block (which can also be electrically assessed after lesioning) is potentially only transient in lesion regions which are functionally inactivated, but not cellularly destroyed. In some embodiments, electrodes configured to make dielectric property measurements are also configured to sense ongoing electrical activity, allowing at least partial determination of electrical block according to a sensed loss of activation. However, regions which retain cellular integrity potentially recover from lesioning. This can make it difficult to functionally assess long-term procedure results immediately post-lesion based on determination of electrical block alone. Recovery from functional electrical block can lead to restoration of electrical activity which causes atrial fibrillation to resume. Potentially, however—for example, since some mechanisms determining tissue dielectric properties depend on intact cell membranes—dielectric assessment can distinguish between merely inactivated tissue, and tissue wherein cellular structure itself has been compromised. Potentially, it is an advantage to rapidly detect a gap or potential gap in irreversibly ablated tissue. Optionally, ablation can be continued and/or re-routed in response. Potentially, this is done before the full development of post-ablation tissue changes, such as edema, which can interfere with outcome of further ablation attempts. For example, post-ablation dielectric property measurement is performed after ablation completes within an interval of 100 msec, 1 second, 10 seconds, 20 seconds, or another larger, smaller, or intermediate interval.

It should also be noted that functional assessment of lesion block as such (for example, assessment of electrophysiological transmission into the left atrium from a pulmonary vein) is potentially time consuming—it can involve repositioning of electrodes and/or infusion of a substance such as adenosine. In this respect, dielectric lesion assessment provides the potential advantage of lesion assessment immediately or almost immediately upon completion of lesioning.

Dielectric measurement-based lesion assessment is optionally performed before, during, and/or after ablation. Before lesioning, such assessment can help with ablation planning, positioning, safety, and/or help to assure that lesioning does not begin until conditions are likely to allow complete lesioning to occur. During lesioning, such assessment (used, for example, in feedback control of lesioning) can help assure that lesioning continues to completion, is terminated before an unsafe condition occurs, and/or is guided through a series of intermediate stages which avoid unsafe conditions and/or help to shape the lesion as desired. After lesioning, such assessment can be used to verify that lesioning has occurred as planned—or if not, can be performed quickly enough that more ablation can be applied before the full development of injury response conditions that could later interfere with lesioning (for example, as edema).

Assessment of lesion properties during or after lesion formation also provides a potential advantage over index-based methods incorporating results of contact-force measurement. While contact-force during lesioning has been shown to have some correlation with results obtained, it does not itself comprise a measurement of those results. Dielectric measurement lesion assessment potentially allows closing a feedback loop with respect to expected and achieved lesioning results.

In some embodiments, dielectric property measurements in support of lesion treatments for other disease conditions are performed. For example:

Hypertrophic obstructive cardiomyopathy (HOCM) ventricular outflow tract ablation is performed, in some embodiments, to reduce a volume of tissue which is blocking blood outflow from the heart. Optionally, dielectric property measurement is used, for example, in planning, ablation, and/or assessment.

In some embodiments, ablation by neuromodulation is performed. Optionally, dielectric properties of target neural tissue are used to distinguish ablation target locations, guide of ablation (for example, if a limited ablation is to be performed, it is a potential advantage to have feedback to guide stopping conditions) and/or verify ablation.

In some embodiments, ablation is used in oncological situations, such as reduction of tumors and/or control of metastasis. It is a potential advantage for positioning, planning, and verification to assess the presence of dielectric properties associated with cancerous growths.

In some embodiments, dielectric properties associated with tumors of various types are maintained in and/or referred to an oncology database, potentially allowing dielectric property-based inferences such as tumor state, prognosis, and/or preferred treatment to be made.

Frequencies found to be useful in distinguishing tumors include those around 1 MHz, for example.

The flowchart of FIG. 3 begins from a time after preparation of a patient and introduction of one or more probes to a target tissue region (preferably via catheter); for example, after block 204 as described in relation to FIG. 2.

The probes optionally comprise an ablation probe and a measurement probe; optionally, the two probes are the same probe.

At block 302, in some embodiments, the flowchart starts, and an initial state of tissue in contact with a measurement electrode and targeted for ablation is optionally determined. The initial state determination optionally is used as a baseline in the selection and/or guidance of ablation to produce a target result.

In some embodiments, the initial state comprises a thickness, determined by measurement; for example, manually by the user via a user interface, automatically according to previously acquired anatomical data, and/or automatically based on one or more dielectric property measurements. Thickness, in some embodiments, is calculated from one or more anatomical images of the patient (e.g., left atrial wall thickness—LAWT, is calculated from a patient's CT image). Optionally, tissue thickness defines the extent of allowed and/or targeted ablation (fully or partially transmural ablation, for example).

In some embodiments, the baseline state used comprises assessment of another property of the tissue, for example, assessment for fibrotic condition (e.g., pre-existing treatment- or disease-caused lesions).

In some embodiments, the baseline state used comprises assessment of contact quality with the tissue. Optionally, contact quality is determined based on the dielectric properties of the tissue environment of the contacting electrode (good contact is considered to exist, for example, when the dielectric properties measured match those of contacted myocardial tissue, rather than blood). Optionally, contact quality is a function of contact force. It should be noted that use of dielectric properties for contact quality assessment has a potential advantage over use of contact force as such, for example, by being substantially independent of contact angle.

In some embodiments, determination of baseline state based on dielectric property measurement includes referencing measured impedance characteristics to a dataset correlating impedance characteristics Z with tissue characteristics Y.

Optionally, the referencing comprises consideration of measured and/or calculated values for other conditions, for example as described in relation to FIG. 2, blocks 209 and 211. For example, dielectric properties of nearby tissues inferred from imaging scans are modeled to assist in isolation of measurement components relating to the tissue to be lesioned. Also for example, initial state determination 302 optionally includes determination of phase of cardiac cycle and/or phase of respiratory cycle. Potentially, this allows dielectric property measurements to be referenced with respect to being of contracted or relaxed tissue, or with respect to a time-varying quality of contact between tissue and probe electrode due to cyclic motions.

In some embodiments, the determination of baseline state is based on dielectric property measurements, optionally without interpretation as representation of a specific physical state such as a thickness or fibrotic condition.

For example, analysis of a calibration dataset optionally establishes a collection of vector correlations. In some embodiments, a baseline state vector $X(t_0)$ derived from initially determined dielectric and other properties is linked to the production of a target lesion state $Y(t_n)$ in the data structure. Then it is optionally omitted to describe the tissue initial state in terms of structural properties such as thickness; instead the measured dielectric state is the baseline. At block 304, in some embodiments, planning of ablation is performed.

In some embodiments, planning of ablation is according to previously determined correlations between measurement state vectors X and target lesion state vectors Y. For example, a baseline state is linked to a target state through a planned ablation protocol, which previous calibration has shown potentially capable of transforming the initial state toward the target state.

The transformation is optionally through multiple stages. For example, the transformation is optionally be through the planned and/or feedback-guided application of ablation energies that evolve the target site through a sequence of dielectric/other condition state vectors $X(t_1) \ldots X(t_n)$, by what may be considered as a series of incremental ablations applied between t=1 and t=n (optionally discretely or continuously applied), where the calibration dataset substantially identifies measured state $X(t_n)$ with a measured state correlated with target lesion state $Y(t_n)$.

In some embodiments, ablation is applied under feedback control. For example, ablation parameters are adjusted after at least one measured intermediate state $X(t_i)$; optionally, after multiple such state measurements. Optionally, the adjustment comprises stopping ablation (for example, if $X(t_i)$ is correlated to a finished ablation state, or to a state which indicates a possible existing and/or developing adverse condition). Optionally, the adjustment comprises an effective increase or decrease in delivered energy, for example to speed up or slow down a rate of ablation.

Alternatively, open-loop application of ablation is planned: e.g., a certain ablation protocol applied to tissue in state $X(t_0)$ is expected, based on results gathered when accumulating the calibration dataset, to produce target lesion state $Y(t_n)$.

In embodiments where ablation parameters are determined and/or controlled based on one or more measurements of X(t), the corresponding lesion state(s) of Y(t) (optionally describing such parameters as lesion depth, volume, and/or width) are optionally either estimated or not. However, it is preferable (as well as being practically likely) that the calibration dataset allows estimation of Y(t) for at least some values of X(t) detected during ablation, as well as in the target ablation state.

Additionally or alternatively, in some embodiments, a simulated ablation is optionally selected (e.g., from a dataset of such simulations) based on the determined initial state. The simulation is calculated, for example, using a model, based on experimental data (such as the calibration dataset), and/or based on thermodynamic equations.

Optionally, the simulation is of ablation according to a location of an ablation probe. The location may be the real-time location of the ablation probe, a simulated location, or any other location thereof. Optionally, the simulation is performed according to a simulated optimal contact force between the distal end portion of the simulated probe and tissue in proximity to the target tissue. Optionally, the simulation is performed according to a current estimated contact force. Optionally, the simulation of the ablation is according to one or more ablation parameters (e.g., voltage, current, power, frequency, and/or ablation electrode surface area dimensions).

It should be noted that in some embodiments, selection of a simulation for ablation of target tissue is (alternatively or additionally) part of a pre-planning phase (that is, planning before catheterization begins) used to select parameters such as measurement and/or ablation probes, the ablation frequency and power for use with ablation probe, etc. Optionally, the simulation provides the user (e.g., physician) with a forecast success criterion of the simulation to enable the user to select these parameters. The process of selection, simulation, and forecast is optionally iterated until optimal projected results are obtained.

In some embodiments, simulation itself is performed at the time of selection (for example, during ablation, and/or pre-planning).

In some embodiments, one or more additional safety and/or success checks are performed before ablation itself begins. For example, a user may have set a lesion requirement (such as a transmural, permanent lesion), which current conditions do not allow the apparatus to achieve, or place it at elevated risk of not achieving, based on simulation and/or available pathways determined from the calibration dataset.

Optionally, in such a case, the system alerts the user to this state, and/or refuses to begin the ablation (optionally refuses without receiving an override). This is a potential advantage, since, for example, a "partial" result could lower the efficacy of the treatment, or path to a "full" result could result in encountering an unsafe or preferably avoided condition such as charring and/or steam pop. Partial ablation, for example, potentially creates edema associated with increased likelihood of failure on a subsequent iteration to correct the problem. For example, edema potentially raises energy requirements for ablating a region. It should be noted, however, that in some embodiments, partial ablation, if it nevertheless occurs, is potentially assessed by dielectric measurements quickly enough after lesioning that a further lesioning cycle can be re-entered before edema fully develops. A more acceptable result could be achieved, for example, after a brief pause for cooling, and/or a small probe movement before "finishing" a lesion site. In this connection, it should be noted that edema can make it difficult to accurately sense ablation state, even dielectrically, after a long enough intervals post-ablation (for example, after about a minute or two).

Additionally or alternatively (for example, when the determination of a potential adverse state is during pre-planning), a system detecting a problem in meeting a lesion requirement provides an alternative approach to achieve the desired result. For example, the system allows and/or suggests changing an energy source, catheter, and/or catheter tip angle to tissue. In some embodiments, the system allows and/or suggests an alternative line of ablations bypassing the difficult region, preferably while avoiding introduction of an ablation line gap.

At block 306, in some embodiments, a processor operating under the control of processing code receives one or more measurements of the values of one or more dielectric parameters of tissue in proximity to the target tissue and/or including the target tissue (for example, as describe herein in relation to FIG. 2). The measurement is optionally of the myocardium, tissue in contact with the catheter ablation element and/or other tissue (e.g., blood). The measurement may be carried out by one or more probe electrodes.

Optionally, measurement(s) are performed before an ablation of the target tissue (e.g., for ablation planning), during the ablation (e.g., to iteratively adjust the ablation planning based on dielectric measurement results), and/or after the ablation of the target tissue (e.g., to assess ablation results).

Dielectric measurements are optionally performed at two or more frequencies (for example, up to about ten frequencies), using one or more probe electrodes and/or electrode patches, according, for example, to parameters described in relation to FIGS. 1A-B.

In some embodiments, a result of the measurements at block 306 in time t is a time-dependent measurement vector $X(t)$, comprising impedance measurement data. At block 308, in some embodiments, the next ablation period is optionally planned, based on information available, pre-planned ablation parameters, and/or an ablation result target.

In some embodiments, a processor operating under the control of processing code uses the last measured state vector $X(t)$ to select a corresponding lesion state vector $Y(t)$ based on correlations determined in the calibration dataset. Selection of a target lesion state vector allows estimation of lesion volume, lesion depth, lesion extent, lesion transmurality, lesion state (edematous, for example) and/or another lesion parameter, according to the components of state vector $Y(t)$ and/or other parameters estimable therefrom. In some embodiments, components of the state vector $Y(t)$ include and/or include information for estimation of a parameter related to safety and/or adverse states. For example, a current risk and/or likelihood of charring, steam pop, wall perforation, or another preferably avoided condition is estimated.

In some embodiments, a processor operating under the control of processing code processes a time history of vectors $X(t)$ and/or $Y(t)$ to estimate an incipient (for example, developing or potential) safety-related condition. For example, if it is predicted that a safety issue such as charring is likely to arise before a lesion spreads adequately from the lesion focus (e.g., by thermal conduction), a rate of ablation energy delivery is optionally reduced. This is optionally before an actual adverse safety condition is determined which could, in some embodiments, force shutdown of the ablation procedure before completion.

In some embodiments, the planning of the next ablation period at block 308 includes a "continue/don't continue" determination, according to which the decision branch at block 310 is optionally selected. For example, if the target state $Y(t_n)$ has been reached, ablation stops. In some embodiments, one or more additional criteria are used as stop conditions; for example, a maximal allowed ablation time or a temperature safety threshold. Optionally, the user stops ablation manually. Optionally, the dielectrically measured progress of ablation, and/or one or more parameters of the ablation such as elapsed time and/or temperature are indicated to the user, for example, as one or more displays, tones. The operator optionally decides to continue or stop ablation, based on such indications.

Additionally, in some embodiments, ablation parameters $L(t)$ themselves are dynamically determined. For example, power is optionally reduced or increased, power frequency shifted, and/or power pulsing adjusted, in order to make achieving the targeted lesion result more likely. In an example, ablation power is reduced to avoid overheating tissue near an ablation electrode before heat has a chance to distribute to nearby tissue. In another example, RF ablation frequency is changed to a frequency which is less effectively absorbed by tissue. Again, this potentially allows thermal transfer time to distribute heat more evenly to avoid localized overheating.

In some embodiments, determination of $L(t)$ is with respect to one or both of measured properties vector $X(t)$ and associated result vector Y(t). For example, energy delivery is optionally selected to avoid undesirable (predicted) values of Y(t). Additionally or alternatively, energy delivery is optionally adjusted to bring the time-evolving (measured) values of X(t) into a region of dielectric property state space where statistical associations of measured dielectric properties with lesion results are more predictable, and/or where the measurements themselves are more reliably adjusted toward a target state.

A potential advantage of such an approach is to reduce the region of state space over which calibrations need to be performed. Optionally, a main "trunk" of correlations between dielectric parameter and lesion results is established for a given system configuration, within and along which results are reliable, and a rich statistical history can be generated. When a vector value of X falls on this trunk, it is then statistically clear how to iteratively apply ablation parameters to get it to a target state. When X falls away from the trunk (for example, on a more sparsely sampled region of the state space), the well-sampled trunk is optionally treated as an attractor. Ablation parameters are adjusted to those statistically most likely to move the currently measured state toward some region of the reliably sampled trunk (exactly where in the trunk may or may not be easily controlled). Once entering this more reliable region, however, better available statistics potentially allows more reliable "navigation" of the measured state to the state associated with the target result state, by application of ablation parameters.

Optionally, an ablation electrode is dragged across tissue during an ablation. Optionally, an operator changes ablation electrode position during dragging based on a dielectric property feedback (slower or faster, for example, depending on local ablation state). In some embodiments, automatic assessment of current ablation state and/or ablation planning for a next period of ablating incorporates information about the position and/or position history of an electrode on the tissue. For example, a maximum allowed ablation duration is extended if the ablation electrode has moved. Additionally or alternatively, recognition that the electrode has moved during ablation is taken into account as an "explanation" of what might otherwise appear to be an exceptional condition wherein ablation progress is not commensurate with what is expected based on ablation energy delivered.

At block 310, in some embodiments, a determination is made as to whether further ablation is required. This is based, for example, on the planning of block 308. Additionally or alternatively, a user can decide to stop ablation manually. If ablation is stopped, the flowchart stops.

Otherwise, ablation continues at block 312, according to the current ablation parameters. Optionally, ablation parameters are constant; alternatively, they are set, for example, according to descriptions herein (with respect to FIG. 2, for example) of ablation parameter vector L(t). In some embodiments, at least one electrode which is used for lesion assessment is also used to supply ablation energy (for example, RF ablation and dielectric lesion assessment are performed with same electrode). In some embodiments, electrodes used for lesion assessment are separate from the electrode or other probe element which causes ablation. It is a potential advantage for ablation and assessment electrodes to be the same, since this potentially allows the closest coupling between the two.

Optionally, measurement continues in another iteration of the loop at block 306.

Figure 4:
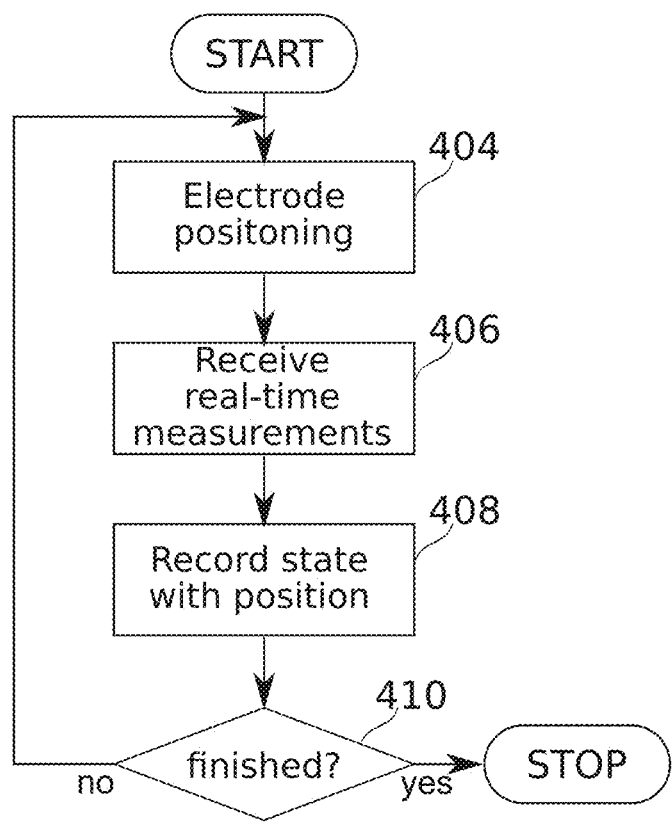
FIG. 4 is a schematic flowchart of a lesion mapping process, in accordance with some embodiments of the present disclosure.

In some embodiments, ablation is open loop—for example, there is just an initial determination of measurement state and ablation plan, which is carried out at block 312 before the procedure terminates. Reference is now made to FIG. 4, which is a schematic flowchart of a lesion mapping process in accordance with some embodiments.

In some embodiments, a lesion mapping process is performed, comprises assessment of lesioned and unlesioned regions over an extended tissue area (such as a left atrium wall). Optionally, lesion mapping comprises a procedure separate from lesion formation as such. For example, an operator optionally maps a general region before or after lesioning at one or more specific foci. Before lesioning, this mapping can be, for example, to determine what the general state of tissue is—for example, to assess a baseline dielectric property map, to localize a lesion (e.g., a lesion track) which has been previously created, and/or to map disease-related lesions such as fibrotic heart regions. Additionally or alternatively, lesion mapping is performed after lesion formation, in order to verify the overall structure of the lesions which have been created—for example, to identify potential gaps between lesions, through which pulmonary vein reconnection could potentially occur.

At block 404, in some embodiments, the flowchart begins, and one or more measurement electrodes are brought to a first position. Position is optionally monitored by any suitable method, for example, by radiographic monitoring, electric field-based position monitoring, magnetic field monitoring, or another method. In some embodiments, position monitoring is at least partially dependent on the measurement of dielectric properties itself; for example, position in contact with a myocardial wall is verified based on dielectric properties.

At block 406, in some embodiments, real-time measurement of dielectric properties at the position or positions of the electrodes is made, for example as described herein in relation to FIGS. 1A-B.

At block 408, in some embodiments, dielectric properties and position are correlated, and added to a (spatial) map of such properties. Additionally or alternatively, dielectric properties are converted to another mapped state (for example, estimated lesion depth, fibrotic state, or another state), and correlated to electrode position. The conversion is based, for example, on a data structure 130, as described herein.

At block 410, a determination is made as to whether or not mapping is to continue. If not, the flowchart stops. If yes, the flowchart continues at block 404, with the electrodes being moved to a new position.

It should be understood that such mapping is optionally performed continuously based on any position/dielectric property data received by the system, even during a phase of planning or lesioning. A potential advantage of this is to increase the fluidity/transparency of procedure work flow. For example, even as a dragged or multi-focal lesion track is being formed, a user optionally drags sensing electrodes around to map or re-map the current situation. This can be an advantage for dynamic planning and/or re-planning.

Lesion Formation for Treatment of Atrial Fibrillation

Reference is now made to FIGS. 11A-11C, which schematically illustrate aspects of lesioning to block of tissue conduction, for example for the treatment of atrial fibrillation, according to some exemplary embodiments of the present disclosure.

In some embodiments, ablation treatment of a tissue region 50 (for example, cardiac tissue of the atria) comprises the formation of a substantially continuous lesion of tissue which serves as a block to conduction. In some embodiments, the targeted region of block is along a lesion path 54 formed from a plurality of sub-lesions 52 arranged along it a substantially contiguous fashion. Shown in FIGS. 11A-11B, for example, is a lesion path 54 which encircles two pulmonary veins 48 of a right atrium (a view from inside the atrium is shown).

In some embodiments, an catheter probe 111 comprising at least one electrode 103, acting as an ablation electrode, is moved sequentially along path 54, ablating at a plurality of locations to create a chain sub-lesions 52 at each location. In some embodiments, electrode 103 also acts as a sensing electrode for dielectric properties of the tissue near it. Optionally ablation is by another probe, for example a probe operating alongside and/or in alternation with electrode 103 operating as a sensing electrode for dielectric properties.

Effective blockage treatment of an irregular impulse conduction disease such as atrial fibrillation potentially fails when the blockage is broken or incomplete. In FIG. 11B, impulse 55 is shown arising from the vicinity of a pulmonary vein 48. Where it encounters a completed lesion 52 (for example, at boundary 55A), conduction is stopped. However, a gap 52B potentially allows the impulse 57 to escape into surrounding tissue, where it may contribute to an irregular heartbeat. The minimum size of a gap allowing conduction can be, for example, about 1.0 mm, 1.3 mm, 1.5 mm, or another larger, smaller or intermediate value. Examples shown and discussed herein (For example, in relation to FIGS. 6A-10H) also illustrate examples of ring-like lesion patterns in cardiac tissue (although formed ex vivo), some of which also include partial or complete gaps.

FIG. 11C illustrates how sensing of lesion depth relates to determination of a potential for relatively effective or ineffective conduction block. Tissue region 50 is shown with a chain of lesions 52, 52A, 52D, 52C already formed. The various depths of these lesions are schematically outlined as dotted line paraboloids 53.

Electrode 103 is shown in contact with a surface of tissue 50, over lesion and targeted tissue area 52C. Here, the lesion is transmural, to the degree that it has begun to spread across the opposite surface of tissue 50 at region 53C. Optionally, electrode 103 senses dielectric properties at this region. Based, for example, on previously determined correlations between dielectric properties and tissue state, it is optionally determined that a fully transmural lesion has been produced, and that no further concern need be taken. If the electrode 103 were placed to target lesion 52A, it would still optionally detect dielectric properties consistent with a deep lesion, but the degree of transmurality is potentially lower (for example, a small distance 53A has been left). This may not be a reason for concern, if gap 53A is too small to allow impulse conduction.

However, at lesion 52D, the lesion is too shallow, and gap 53D is sufficiently large to allow impulse 57 to pass through it. Optionally, electrode 103 detects dielectric properties of the tissue here which are consistent with the dielectric properties of an incomplete lesion. Optionally, determination of this comprises comparison of the dielectric properties measured with a data structure describing correlations between dielectric properties and lesion depth. Optionally, the comparison is facilitated by inclusion in the comparison of anatomical properties such as wall thickness—optionally known or inferred, for example, from separate measurements (e.g., imaging), from the dielectric measurements themselves, and/or with reference to more general anatomical knowledge such as anatomical atlas data.

Examples of Lesion Assessment

Figure 5A:
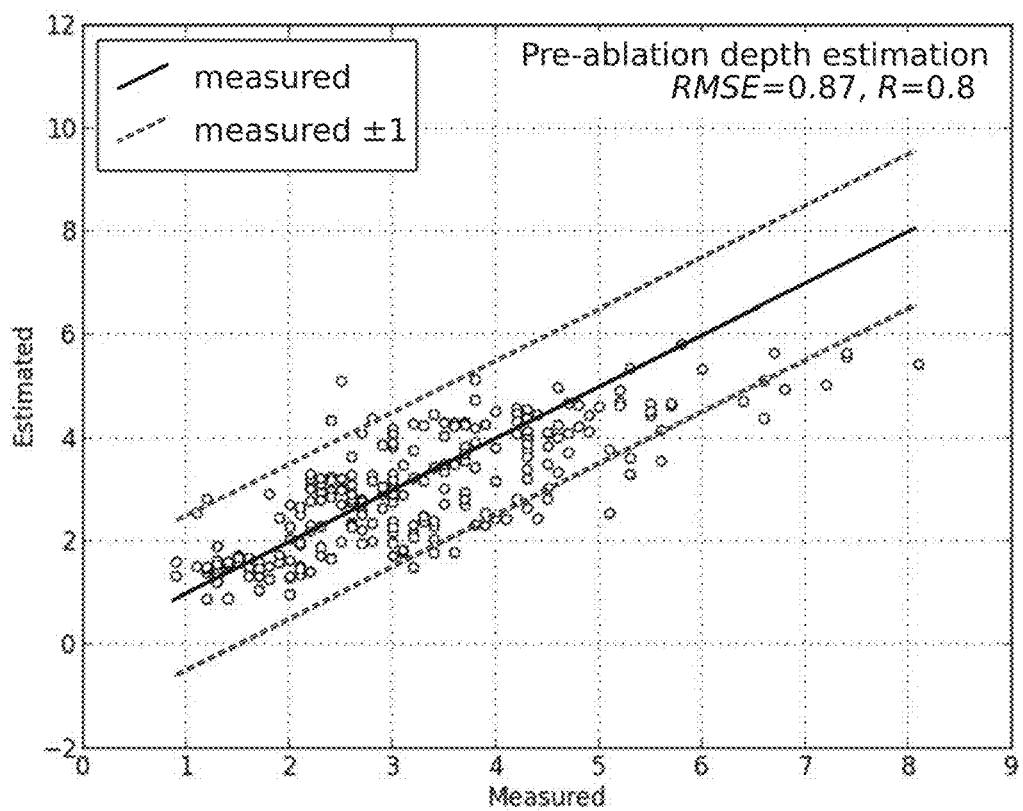
FIGS. 5A-5B graph estimated vs. measured depths of planned or completed ablation, in accordance with some embodiments of the present disclosure.
Figure 5B:
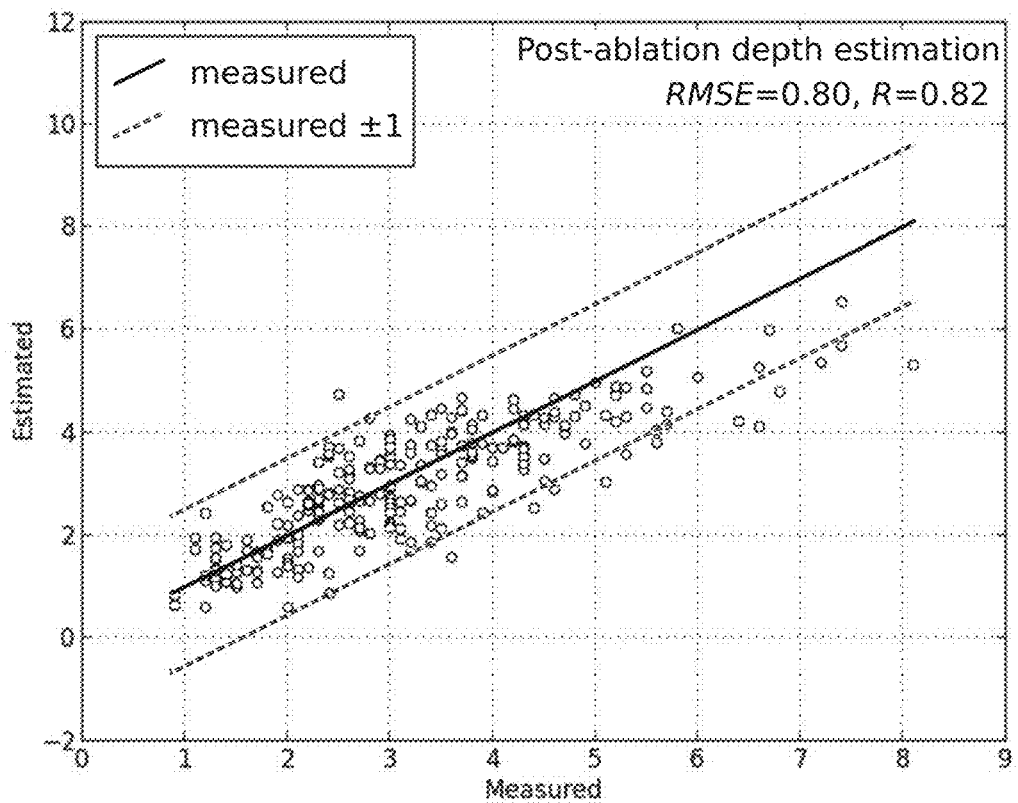

Reference is now made to FIGS. 5A-5B, which graph estimated vs. measured depths of planned or completed ablation, in accordance with some embodiments.

Figure 9A:
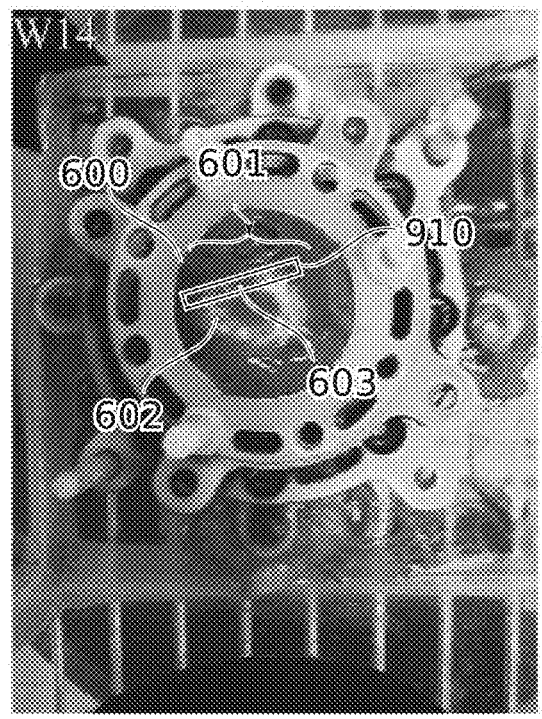
FIGS. 9A-9C show a color-stretched photograph of a lesioned ex vivo porcine heart wall preparation (FIG. 9A), as well as two micrographs (FIGS. 9B-9C) corresponding to sections through the preparation, in accordance with some embodiments of the present disclosure.
Figures 9B, 9C:
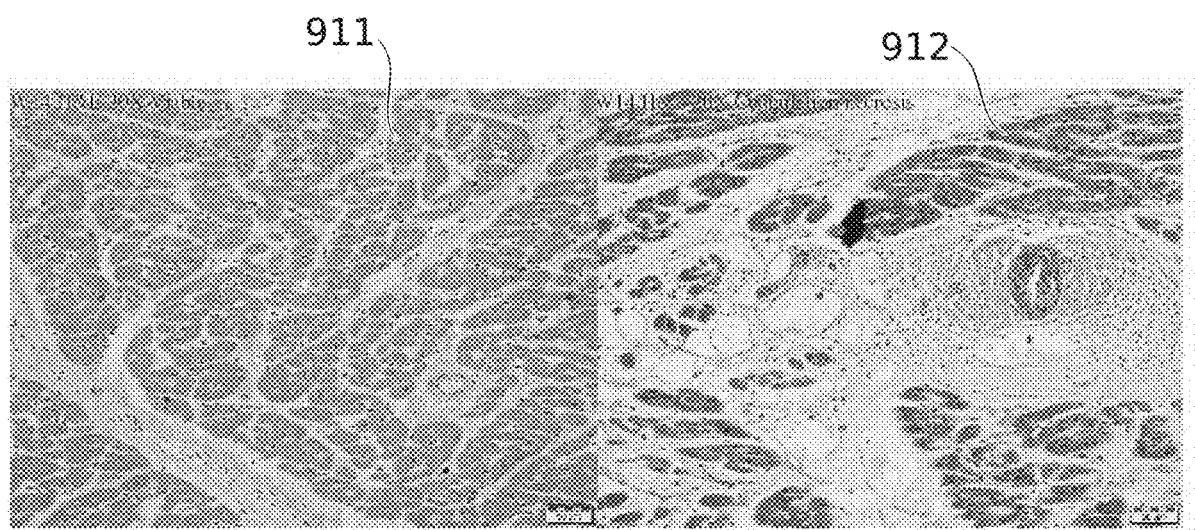

The graphs of FIGS. 5A-5B represent data acquired using an ex vivo porcine right ventricle heart wall preparation similar to that shown sectioned in FIG. 9B.

Lesioning was performed according to clinically relevant parameters for generating transmural atrial wall lesions. For example, under RF ablation, about 20 seconds of ablation per lesion focus site was performed at about 30 W power, using an RF frequency of about 500 kHz. In some examples shown herein (for example, non-transmural lesions of FIGS. 6A-6T, 7A-7G, or 10A-10H), lesion time and/or power was deliberately reduced for some foci.

Estimated depths in FIG. 5A (ordinate axis) were obtained based on dielectric measurements by electrodes in contact against non-lesioned heart wall tissue. Estimations represent values predicted from pre-ablation dielectric measurements by a trained classifier, while measured values represent lesion thicknesses measured from tissue sections. In some embodiments, a classifier (for example, an artificial neural network-based classifier) is trained on a training set of at least a few thousand samples (for example, about 5000, 10000, or another, larger, smaller, or intermediate number of samples). Classification is optionally based on continuous thickness data, which provides a potential advantage relative to methods which select lesioning protocols based on discontinuously categorized thickness data (for example, categories comprising bins centered around 3 mm, 4 mm, and 5 mm thicknesses).

Estimated depths in FIG. 5B (ordinate axis) were obtained based on dielectric measurements by electrodes in contact against lesioned heart wall tissue. Estimations represent values predicted from pre-ablation dielectric measurements by a trained classifier while measured values represent lesion thicknesses measured from cut tissue sections.

In both cases, most estimations were within 1 mm of the value measured in section. It should be noted that the post-ablation estimations have a smaller root mean squared error (RMSE) than the pre-ablation estimations, and a higher linear correlation based on r-value (R).

Reference is now made to TABLE 1, which summarizes experimental results from in vivo ablation experiments in porcine heart. Lesioning was performed using an RF ablation catheter in vivo. An estimator was applied to dielectric property data taken pre-lesioning and/or post-lesioning, to estimate whether a resulting gap in transmurality was within some permissible range (permitted non-transmurality gap). True positive rates (TPR) and False positive rates (FPR) are given for both a post-lesion estimator alone, and for an estimator combining pre-lesioning data with post-lesioning data.

TABLE 1

| PERMITTED NON-TRANSMURALITY | POST ESTIMATOR = 1 (112 SAMPLES) | | PRE = 1 + POST = 1 (51 SAMPLES) | |
| --- | --- | --- | --- | --- |
| GAP (MM) | TPR (%) | FPR (%) | TPR (%) | FPR (%) |
| 0.3 | 92 | 37 | 96 | 45 |
| 0.55 | 90 | 31 | 94 | 37 |
| 0.8 | 89 | 30 | 91 | 35 |
| 1.05 | 82 | 32 | 88 | 37 |
| 1.3 | 77 | 32 | 84 | 38 |

Figure 14:
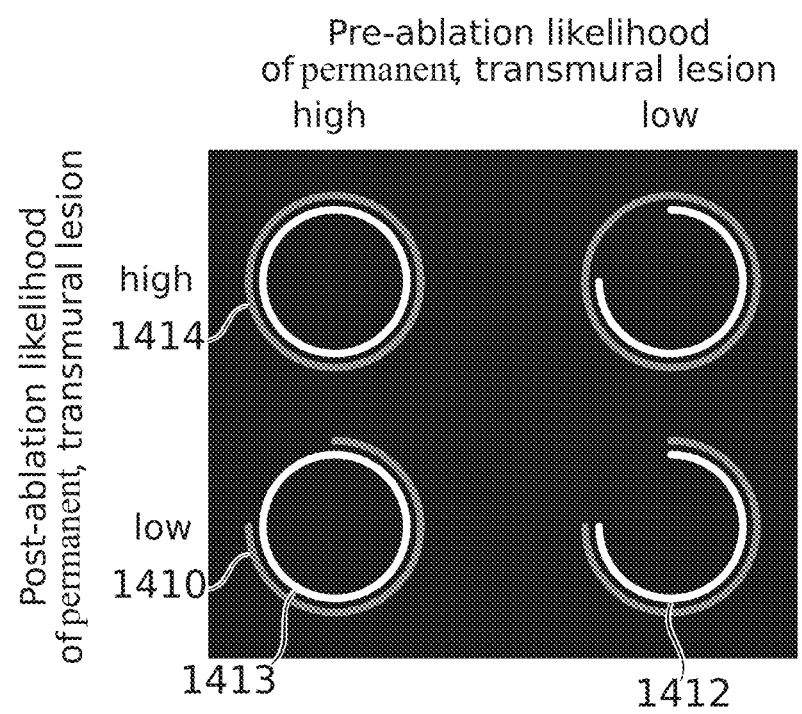
FIG. 14 illustrates display elements which are optionally used to indicate estimated transmurality of a lesion to a user, based on pre- and post-lesioning dielectric property measurements.

Reference is now made to FIG. 14, which illustrates display elements 1410, 1412, 1413, 1414 which are optionally used to indicate estimated transmurality of a lesion to a user, based on pre- and post-lesioning dielectric property measurements.

In some embodiments, estimated transmurality is communicated to a user by the use of a simplified graphical element. The elements of FIG. 14 take the form of complete circles 1413, 1414, to indicate a positive estimate of lesion transmurality, and the form of incomplete circles 1412, 1410 (e.g., ¾ circles) to indicate a negative estimate of lesion transmurality. Optionally, inner circles 1412, 1413 are used to indicate estimates based on pre-lesioning measurements. Optionally, outer circles 1410, 1414 are used to indicate estimates based on post-lesioning measurements.

Reference is now made to FIGS. 6A-6T, which show pairs comprising surface dielectric measurement plots alongside photographs of corresponding lesion patterns, in accordance with some embodiments.

Porcine heart ex vivo heart tissue preparations 600 were subjected to RF ablation in a generally ring-shaped (circular or elliptical) pattern 601 of lesion foci 602. The ring-shaped patterns 601 are similar in size and lesion focus density to a typical pattern used in vivo for the treatment of atrial fibrillation in the vicinity of pulmonary veins. Electrodes corresponding to probe electrodes 103 were placed on the side of the preparations 600 which is shown; the electrodes pared with these electrodes (corresponding, for example, to skin patch electrodes 105) were placed on the other side of the preparation 600.

FIGS. 6B, 6D, 6F, 6H, 6J, 6L, 6N, 6P, 6R, and 6T are photographs (enhanced to emphasize tissue differences by stretching color contrast) of lesion patterns 601. In the examples shown, probes for lesioning and/or measurement are robotically positioned. The distance between each circumferentially adjacent (not gap-separated) lesion focus 602 is about 1 mm.

The plots of FIGS. 6A, 6C, 6E, 6G, 6I, 6K, 6M, 6O, 6Q, and 6S show relative lesion depth corresponding to each photograph, estimated via a trained classifier from dielectric properties measured at multiple locations (for example at frequencies as described in relation to FIGS. 1A-1B) post-lesion.

In color, lighter shading (for example, at region 606) indicates greater lesion depth, and darker shading (for example, at region 608) indicates lesser lesion depth. Lesion foci are shown as circles 604 of different diameters arranged in generally ring-shaped patterns. Circle diameters correspond to degree of transmurality achieved at each lesion focus.

In each of the plots, at least one gap 603 (corresponding to a non- or under-lesioned focus position) has been deliberately left in the lesioning pattern. It should be noted that the dielectric measurement-based plots in each case also show a corresponding gap 605 of reduced lesion depth.

Potentially, such measurements in corresponding in vivo treatment conditions would allow detection of gaps in lesion patterns. Reference is now made to FIGS. 7A-7G, which show two image groups (FIGS. 7A-7C and FIGS. 7D-7G) comprising surface dielectric measurement plots alongside photographs of corresponding lesion patterns, as well as exemplary 3-D plots of lesion depth, in accordance with some embodiments.

Figure 7A:
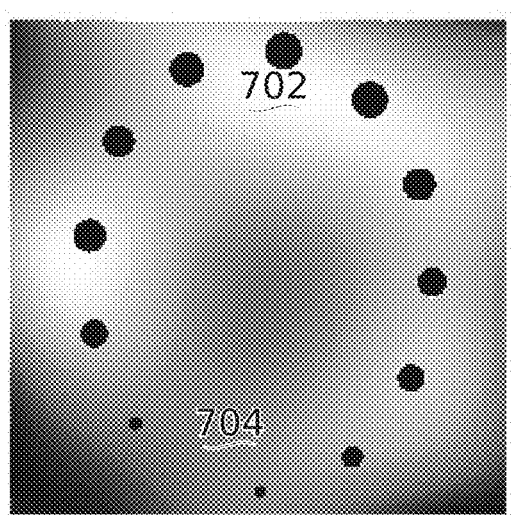
FIGS. 7A-7G show two image groups (FIGS. 7A-7C and FIGS. 7D-7G) comprising surface dielectric measurement plots alongside photographs of corresponding lesion patterns, as well as exemplary-D plots of lesion depth, in accordance with some embodiments of the present disclosure.
Figure 7B:
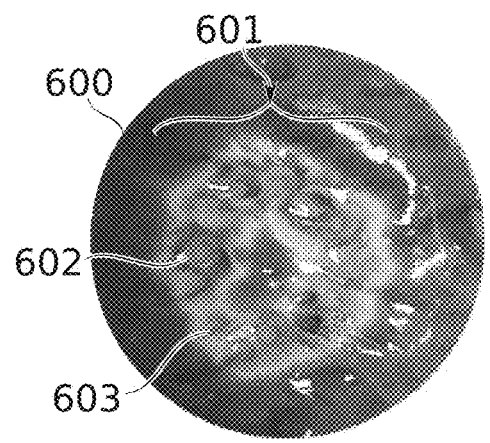
Figure 7C:
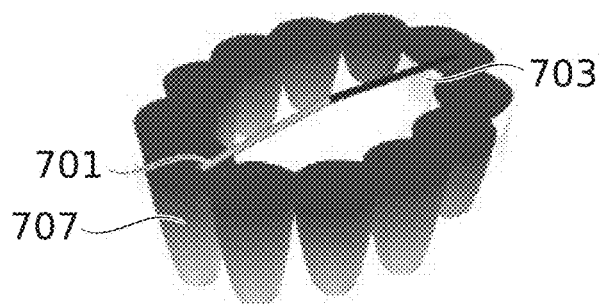
Figure 7D:
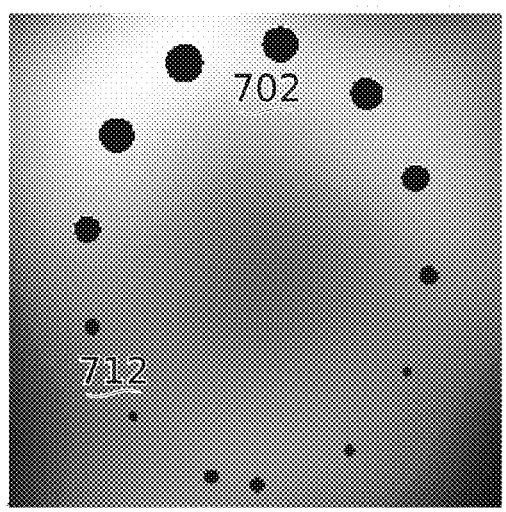
Figure 7E:
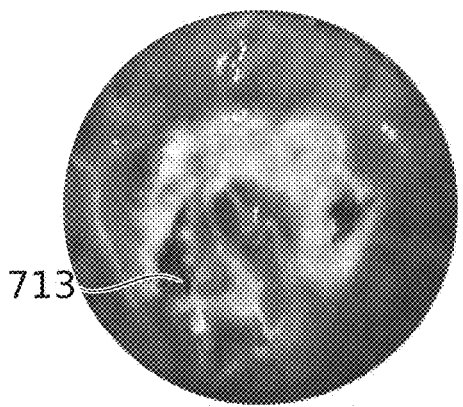
Figure 7F:
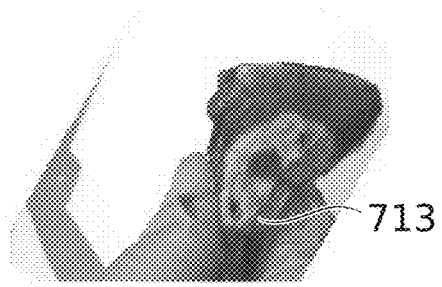
Figure 7G:
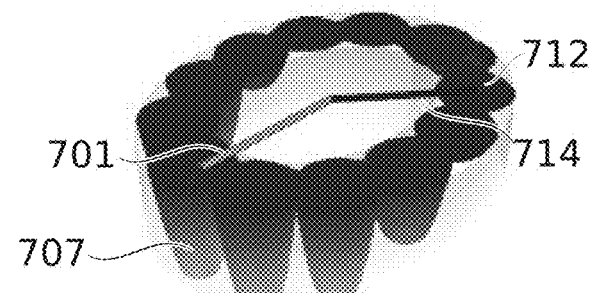

FIGS. 7A and 7D comprise plots of dielectrically determined lesion depth, plotted with conventions and features described, for example, in relation to FIG. 6A. FIGS. 7B and 7E show color-stretched photographs of an ex vivo porcine heart preparation, as described, for example, in relation to FIG. 6B. FIGS. 7C and 7G comprise 3-D plots which correspond to the data shown in FIGS. 7A and 7D, respectively. For example, marker line 701 corresponds to the twelve o'clock position 702 (top center) on FIG. 7A. Marker line 703 corresponds to the "six-thirty" position of the lesion gap 704 (also shown as a gap 603 on FIG. 7B). The size and shape of each of the ring of conical shapes 707 correspond to the corresponding lesion shapes, as inferred from the data of FIG. 7A. In FIG. 7G, the gap center indicated by 712 and by marker 714 is at about eight o'clock, corresponding to gaps 713 of FIGS. 7E and 7F, and 712 of FIG. 7D.

Reference is now made to FIGS. 10A-10H, which are further examples of dielectric measurements of elliptical ablation patterns, according to some embodiments.

In FIGS. 10D-10H, locations of ablation foci and ablation depth at each focus is shown by the location and coloration (darker is shallower, lighter is deeper) of circles 1002. Focus location (but not ablation depth) is indicated by circle 1001 of FIGS. 10A-10C. Ablation foci are arranged in ring patterns, as described, for example, in relation to FIGS. 6A-6B and other figures herein. The ring patterns of FIGS. 10A-10C are gapless, while the patterns of FIGS. 10D-10H have gaps.

Figure 10A:
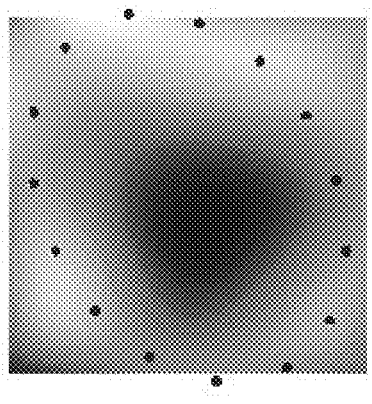
FIGS. 10A-10H are further examples of dielectric measurements of elliptical ablation patterns, according to some embodiments of the present disclosure.
Figure 10B:
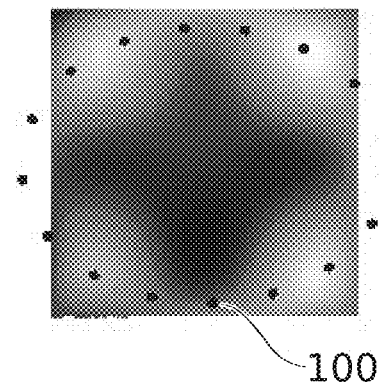
Figure 10C:
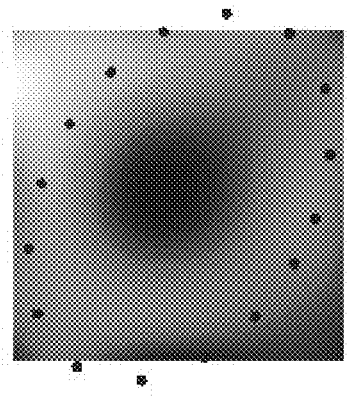
Figure 10D:
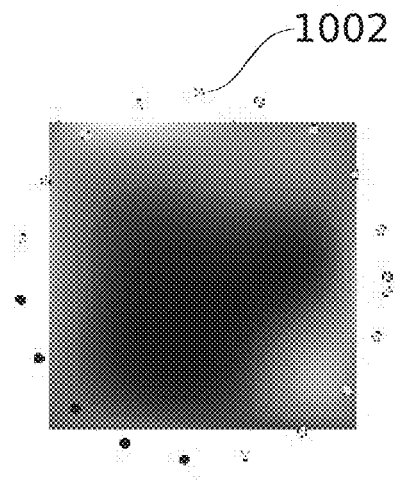
Figure 10E:
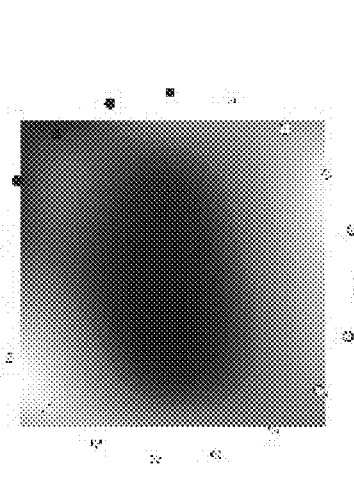
Figure 10F:
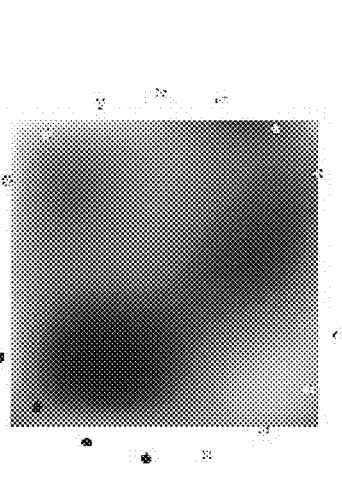
Figure 10G:
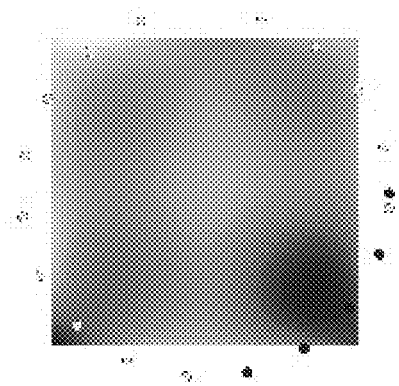
Figure 10H:
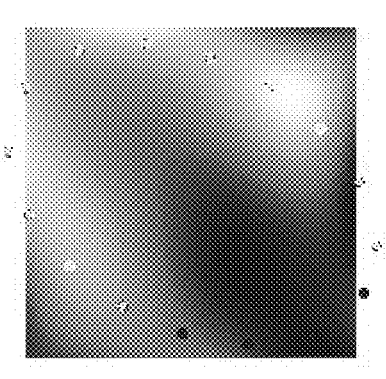

In each of FIGS. 10A-10C, a closed-ring ablation pattern is revealed by the dielectric property depth map. In FIGS. 10D-10H, gaps in ablation depth indicated by darker (shallower) focus circles correspond to darker (shallower) gaps in the dielectric property depth map.

Structure Changes Associated with Tissue Lesions

Figure 8A:
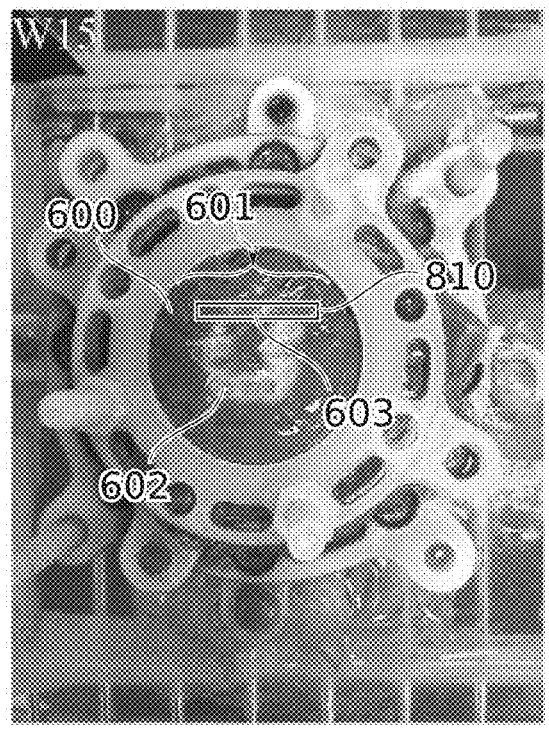
FIGS. 8A-8C show a color-stretched photograph of a lesioned ex vivo porcine heart wall preparation (FIG. 8A), as well as two micrographs (FIGS. 8B-8C) corresponding to sections through the preparation, in accordance with some embodiments of the present disclosure.
Figures 8B, 8C:
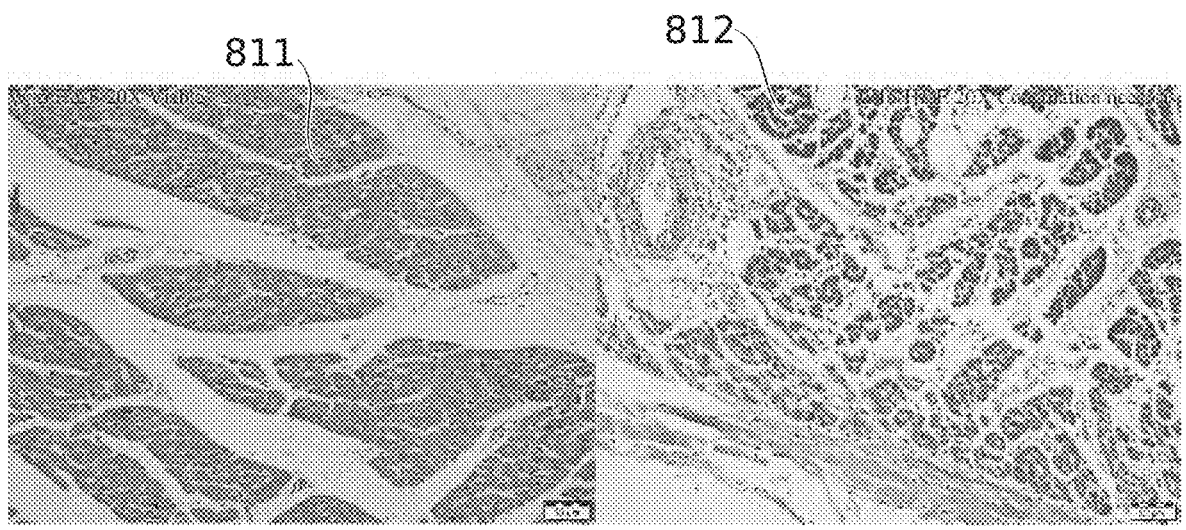

Reference is now made to FIGS. 8A-8C, which show a color-stretched photograph of a lesioned ex vivo porcine heart wall preparation (FIG. 8A), as well as two micrographs (FIGS. 8B-8C) corresponding to sections through the preparation, in accordance with some embodiments. Reference is also made to FIGS. 9A-9C, which show a color-stretched photograph of a lesioned ex vivo porcine heart wall preparation (FIG. 9A), as well as two micrographs (FIGS. 9B-9C) corresponding to sections through the preparation, in accordance with some embodiments.

Cellular details showing microscopic anatomical rearrangement in lesioned vs. unlesioned tissue are illustrative of differences which potentially also manifest as changes in the dielectric characteristics of the tissue. For example, breakdown in the cellular compartmentalization of ions potentially leads to differences in dielectric properties. Condensation of myocardial bands potentially changes the electrical properties of available pathways of current conduction.

Marked regions 810 and 910 indicate the section of the lesion patterns 601 of FIGS. 8A and 9A from which the micrographs of FIGS. 8B-8C and 9B-9C, respectively, are taken.

In FIG. 8A, the lesion pattern 601 comprises a gap 603 in which the lesion exists, but is non-transmural. In FIG. 9A, a full gap has been left in the lesion pattern.

In FIGS. 8B and 9B, regions 811, 911 (for example) show non-lesioned regions of viable myocardium. Myocardial bands, stained dark, fill relatively contiguous regions of the micrograph. FIGS. 8C and 9C shows regions 812, 912, for example, which have been lesioned, with the resulting appearance of coagulation necrosis. For example, myocardial bands are relatively condensed, becoming darker, and opening gaps between them. There is no evidence of extracellular fluid.

Multi-Electrode Phased RF Ablation Catheter

Figure 13:
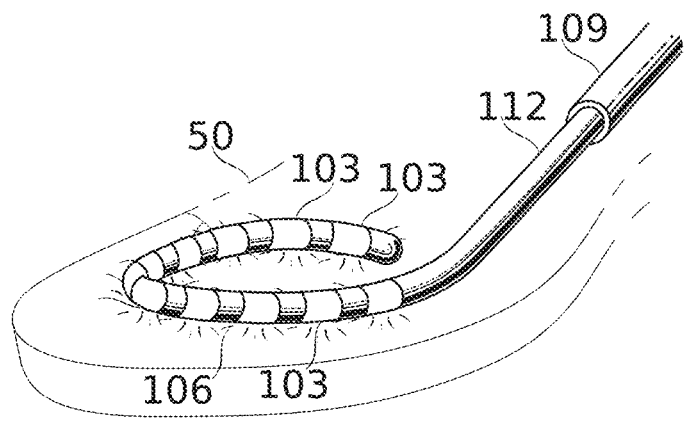
FIG. 13 is a schematic illustration of a multi-electrode catheter probe operable for phased RF ablation in contact with a tissue wall, according to some exemplary embodiments.

Reference is now made to FIG. 13, which is a schematic illustration of a multi-electrode catheter probe 112 operable for phased RF ablation in contact with a tissue wall 50, according to some exemplary embodiments.

In some embodiments, catheter 109 comprises a multi-electrode probe 112 (optionally, with details changed as necessary, a bipolar probe). In the example shown, multi-electrode probe 112 comprises a curvilinear arrangement of ten electrodes. It is to be understood that, optionally, another electrode arrangement is provided: for example, straight, cross-shaped, multi-ribbed, or another configuration of any plurality of electrodes. A potential advantage of the curvilinear arrangement in particular is general conformation to the shape of a lesion which circumvallates a venous root of an atrium, for example.

In some embodiments of the invention, lesioning comprises the delivery of power between different pairs of individual electrodes in a sequence of phases. Suitably selected, this provides potential advantages for the control of lesion form. For example, two different electrode pairs may each heat a shared region between them; switching between pairs may heat this shared region preferentially, while allowing non-shared regions to remain relatively cool due to a lower heating duty cycle. Heating may also be induced to lesion between electrodes already located on a planned lesion line, which has potential advantages for control of position and/or the prevention of the introduction of lesion gaps. In some embodiments, a plurality of electrodes configured to complete a corresponding plurality of circuit paths for RF power applied through one electrode are positioned in different tissue regions such that heating effects are concentrated in the region closest to that one electrode, while the different tissue regions each receive only a relative fraction of the heating effects.

In some embodiments of the invention, pre- during- and/or post-lesioning tissue state assessment is performed as described herein (for example in relation to FIGS. 2-4 and/or 12) for a plurality of sites contacted by the electrodes 103 of multi-electrode probe 112. Optionally, at least one parameter of ablation power and/or timing (for example, duty cycle) is varied for ablation different lesion sites selected by the placement of the electrodes 103 against tissue surface 50. For example, an average power and/or a duration of power is reduced for phases of the lesioning cycle directed to the lesioning of sites which are relatively thin-walled, compared to sites which are relatively thick-walled, or for another reason, for example as described herein. Optionally, a phase difference (e.g., 90°, 45°) between pair(s) of electrodes 103 is varied for ablation different lesion sites, e.g., by obtaining different field patterns.

It is expected that during the life of a patent maturing from this application many relevant ablation methods will be developed; the scope of the term ablation method is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of tissue assessment in vivo, comprising:
determining at least one dielectric property of a target tissue by analysis of signals having a plurality of frequencies, sensed at a plurality of electrodes positioned intra-body, said analysis combining the contribution of a plurality of frequencies, each measured at a plurality of electrodes; and
estimating a tissue state of said target tissue, based on the determined at least one dielectric property.

2. The method of claim 1, wherein the signals comprise signal output from an electrical circuit comprising the plurality of electrodes, each of the plurality of electrodes being positioned at an intra-body position wherefrom the electrode acts in establishing an electrical field intersecting the target tissue.

3. The method of claim 2, comprising planning parameters of an ablating of the target tissue; and wherein:
the estimating comprises prediction of a state of the target tissue, the state predicted to be that state of the target tissue brought about after the ablating is performed according to the parameters of the ablating; and
the parameters of the ablating are adjusted so that the predicted state of the target tissue matches a target state of the target tissue after ablation.

4. The method of claim 3, comprising ablating the target tissue to produce the target state, according to the planning.

5. The method of claim 2, wherein the estimating is further based on estimated anatomical information for tissue affecting the signal output.

6. The method of claim 1, comprising:
receiving a data structure correlating dielectric properties with tissue states; and
wherein the estimating is further based on the received data structure.

7. The method of claim 6, wherein the data structure is obtained by machine learning methods.

8. The method of claim 6, wherein said at least one dielectric property comprises a vector of dielectric parameter values, and said estimating is based on statistical correlation between vectors of dielectric parameter values and said tissue state, the statistical correlation being described by the data structure.

9. The method of claim 1, wherein the determining and the estimating are performed iteratively, during ablating in said target tissue.

10. The method of claim 9, wherein the ablating is controlled based on the estimating.

11. The method of claim 9, wherein at least one of said plurality of electrodes at the intra-body position acts in performing the ablating.

12. The method of claim 9 comprising reducing or terminating the ablating based on the estimating indicating an elevated risk of an adverse event associated with ablating.

13. The method of claim 9, wherein the ablating comprises formation of a lesion in cardiac tissue for the treatment of atrial fibrillation.

14. The method of claim 1, wherein the tissue state comprises at least one from a group consisting of:
a lesion depth; and
a lesion volume.

15. The method of claim 1, wherein the tissue state indicates a state of a lesion formed by tissue ablation.

16. The method of claim 1, wherein the tissue state comprises at least one from a group consisting of:
a physiological tissue property; and
a functional tissue property.

17. The method of claim 1, wherein the tissue state comprises a degree of lesion transmurality.

18. The method of claim 1, wherein the tissue state comprises a characterization of tissue edema.

19. The method of claim 1, wherein the tissue state comprises a characterization of functional inactivation.

20. The method of claim 1, wherein the tissue state comprises a classification as to a potential for tissue charring.

21. The method of claim 1, wherein the tissue state comprises a classification as to a potential for steam pop.

22. The method of claim 1, wherein said determining comprises determining based on signals from a plurality of electrode pairings.

23. The method of claim 1, wherein said plurality of frequencies include 10 frequencies.

24. The method of claim 1, wherein said plurality of dielectric parameters comprises at least four dielectric parameters.

25. A method of tissue assessment, comprising:
receiving a data structure correlating values of dielectric parameters with values of at least one parameter of a tissue state;
determining a value of a plurality of dielectric parameters of a target tissue, based on signal output from an electrical circuit comprising a plurality of electrodes positioned intra-body and in proximity to the target tissue;
estimating a value of at least one parameter of a tissue state, based on the determined value of the plurality of dielectric parameters of the target tissue and the received data structure; and
providing a feedback indicative of said estimate.

26. The method of claim 25, wherein the data structure is obtained by machine learning methods.

27. The method of claim 25, wherein the determining and the estimating are performed iteratively, during ablating in said target tissue.

28. The method of claim 27, wherein the ablating is terminated, based on said estimating.

29. The method of claim 27, wherein at least one parameter of the ablating is controlled, during the ablating, based on the estimating.

30. The method of claim 29, wherein the controlled at least one parameter of the ablating includes at least one of a group consisting of:
- a duration of the ablating;
- a power supplied for the ablating;
- a frequency used for the ablating; and
- selection of an electrode for the ablating.

31. The method of claim 29, wherein the controlled at least one parameter of the ablating includes a rate of ablation.

32. The method of claim 27, wherein the ablating is performed through one of said plurality of electrodes positioned intra-body and in proximity to the target tissue.

33. The method of claim 27, wherein the ablating comprises formation of a lesion in cardiac tissue for the treatment of atrial fibrillation.

34. The method of claim 27, comprising reducing or terminating the ablating based on said estimating indicating an elevated risk of an adverse event associated with ablating.

35. The method of claim 34, wherein the estimating comprises generating an indication of a gap within a lesion formed by said ablating.

36. The method of claim 35, wherein said target tissue comprises a myocardial wall, and said gap comprises a region where the lesion is incompletely transmural.

37. The method of claim 36, wherein said gap comprises a region which is not irreversibly lesioned, the region being at least 1.3 mm across.

38. The method of claim 25, wherein:
- the determining and the estimating are performed before at least a portion of a protocol for ablating of the target tissue is performed;
- the estimating comprises prediction of a value of said at least one parameter of a tissue state, the value predicted as being brought about after said portion of the ablating protocol is performed; and
- the estimating is further based on parameters of the protocol for ablating.

39. The method of claim 38, wherein the feedback comprises an indication of a likelihood of successfully achieving a target lesion result under conditions on which the estimating is based.

40. The method of claim 38, wherein the feedback comprises preventing onset of the ablating.

41. The method of claim 38, comprising adjusting the protocol for ablating of said target tissue, based on the predictive estimating of the at least one parameter of a tissue state; and wherein the feedback comprises providing said adjusted protocol for use in controlling further ablating.

42. The method of claim 38, comprising ablating of a portion of said target tissue.

43. The method of claim 25, wherein the determining and the estimating are performed after ablating of a portion of said target tissue to form a lesion, and the feedback comprises an estimate of the irreversibility of lesioning in a region of said ablating.

44. The method of claim 25, wherein the at least one parameter of a tissue state comprises a lesion depth.

45. The method of claim 25, wherein said value of said plurality of dielectric parameters comprises a vector of values, and said estimating is based on statistical correlation between vectors of dielectric parameter values and said at least one parameter of a tissue state, the statistical correlation being described by the data structure.

46. The method of claim 25, wherein said estimating is further based on estimated anatomical information for tissue affecting the signal output of the electrical circuit.

47. The method of claim 25, wherein the determining comprises analysis of frequency response behavior of the signal output of the electrical circuit.

48. The method of claim 25, wherein the providing comprises providing feedback to control an ablation device.

49. The method of claim 25, wherein said determining comprises determining using signals at a plurality of frequencies.

50. The method of claim 49, wherein said plurality of frequencies include 10 frequencies.

51. The method of claim 25, wherein said plurality of dielectric parameters comprises at least four dielectric parameters.

* * * * *

UNITED STATES PATENT AND TRADEMARK OFFICE
CERTIFICATE OF CORRECTION

PATENT NO. : 10,881,455 B2
APPLICATION NO. : 15/573493
DATED : January 5, 2021
INVENTOR(S) : Yitzhack Schwartz et al.

It is certified that error appears in the above-identified patent and that said Letters Patent is hereby corrected as shown below:

On the Title Page

Item (71) Applicants, Line 2:
Delete the following: "Yitzhack SCHWARTZ, Haifa (IL); Yizhaq SHMAYAHU, Ramat-HaSharon (IL); Eli DICHTERMAN, Haifa (IL)"

Signed and Sealed this
First Day of June, 2021

Drew Hirshfeld
*Performing the Functions and Duties of the*
*Under Secretary of Commerce for Intellectual Property and*
*Director of the United States Patent and Trademark Office*